United States Patent [19]

Kruckenberg

[11] 4,212,803
[45] Jul. 15, 1980

[54] CATIONIC AZO DYESTUFFS CONTAINING OXYALKYLENE SUBSTITUENT

[75] Inventor: Winfried Kruckenberg, Leverkusen, Fed. Rep. of Germany

[73] Assignee: Bayer Aktiengesellschaft, Leverkusen, Fed. Rep. of Germany

[21] Appl. No.: 813,647

[22] Filed: Jul. 7, 1977

[30] Foreign Application Priority Data

Jul. 9, 1976 [DE] Fed. Rep. of Germany ....... 2631030

[51] Int. Cl.² .................... C09B 29/08; C09B 29/26; C09B 29/34; C09B 29/36

[52] U.S. Cl. .................................... 260/154; 260/155; 260/156; 260/157; 260/158; 260/162; 260/163; 260/165; 260/196; 260/187; 260/205; 260/206; 260/207; 260/207.1; 260/207.5; 260/567.6 M; 260/570.5 P; 260/575; 260/577; 260/584 B; 260/584 C; 560/38; 560/186; 560/252

[58] Field of Search .................... 260/157, 158, 207.1, 260/207.5, 154, 155, 156, 162, 163, 152, 187, 196, 207, 206, 205, 165

[56] References Cited

U.S. PATENT DOCUMENTS

| | | | |
|---|---|---|---|
| 2,821,526 | 1/1958 | Boyd | 260/158 X |
| 4,036,826 | 7/1977 | Boemhke | 260/205 |
| 4,051,084 | 9/1977 | Kuhlthau et al. | 260/158 |
| 4,051,117 | 9/1977 | Kuhlthau et al. | 260/146 R |
| 4,072,672 | 2/1978 | Henzi | 260/205 |

*Primary Examiner*—Floyd D. Higel
*Attorney, Agent, or Firm*—Sprung, Felfe, Horn, Lynch & Kramer

[57] ABSTRACT

Cationic dyestuffs of the formula

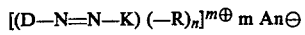

wherein
D denotes the radical of a diazo component,
K denotes the radical of a coupling component,
m and n independently of one another denote 1 or 2,
An⊖ denotes an anion and
R denotes a radical of the general formulae

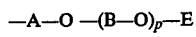

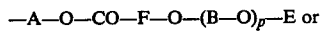

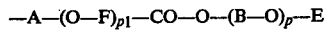

wherein
A represents optionally substituted alkylene with 2 to 4 C-atoms or a direct bond,
B represents optionally substituted alkylene with 2 to 4 C atoms,
E represents hydrogen or optionally substituted alkyl, alkenyl, cycloalkyl, formyl, alkylcarbonyl or alkenylcarbonyl or optionally substituted phenylcarbonyl, phenylalkylcarbonyl, phenoxyalkylcarbonyl, phenylalkyl or phenyl,
F represents alkylene,
p represents 1–3 and
$p_1$ represents 0 or 1,
at least one of the radicals A or B represents substituted alkylene possess good coloristic properties. The dyestuffs are characterized by good water solubility, good fastness to light and to wet processing and have affinity to fibers, as well as good migrating capacity and substantial insensitivity to thiocyanate ions.

10 Claims, No Drawings

CATIONIC AZO DYESTUFFS CONTAINING OXYALKYLENE SUBSTITUENT

As a further development of the inventive concept of Patent Application No. P 25 08 884.0 (German Offenlegungsschrift No. 2 508 884) it has now been found that dyestuffs of the general formula $$[(D-N=N-K)(-R)_n]^{m\oplus} mAn^{\ominus} \quad (I)$$

wherein
D denotes the radical of a diazo component,
K denotes the radical of a coupling component,
m and n independently of one another denote 1 or 2,
$An^{\ominus}$ denotes an anion and
R denotes a radical of the general formulae $$-A-O-(B-O)_p-E \quad (II)$$

$$-A-O-CO-F-O-(B-O)_p-E \quad (III)$$

or $$-A-(O-F)_{p1}-CO-O-(B-O)_p-E \quad (IV)$$

wherein
A represents an optionally substituted alkylene radical with 2 to 4 C atoms or a direct bond,
B represents an optionally substituted alkylene radical with 2 to 4 C atoms,
E represents hydrogen or an optionally substituted alkyl, alkenyl, cycloalkyl, formyl, alkylcarbonyl or alkenylcarbonyl radical or an optionally substituted phenylcarbonyl, phenylalkylcarbonyl, phenoxyalkylcarbonyl, phenylalkyl or phenyl radical,
F represents an alkylene radical,
p represents 1 1–3 and
$p_1$ represents 0 or 1,
and wherein
at least one of the radicals A or B represents a substituted alkylene radical,
possess good coloristic properties.

The radicals R are preferably bonded to a ring carbon atom or to a nitrogen atom of an aminocarbonyl, amino or ammonium group.

Preferred ring carbon atoms, to which R is bonded, are members of an aromatic-carboxycyclic or aromatic-heterocyclic radical, and preferably of a benzene ring, which is linked to the azo bridge.

The cationic charge can be a constituent either of D or of K. The radical F can be linked both to D and to K.

The alkyl radicals mentioned under E can be substituted, for example, by a cyano, halogen or $C_1$-$C_4$-alkoxy radical. The phenyl radicals can be substituted, for example, by 1 or 2 $C_1$-$C_4$-alkyl or $C_1$-$C_4$-alkoxy radical or halogen atoms.

In E, the alkyl and alkylene radicals preferably contain 1 to 6 C atoms and the alkenyl and alkenylene radicals contain 2 to 6 C atoms and can be straight-chain or branched. Cycloalkyl in particular represents cyclopentyl and cyclohexyl which are optionally substituted by methyl.

The radicals A and B are, in particular, substituted by halogen, preferably chlorine; hydroxyl, $C_1$-$C_4$-alkoxy or $C_1$-$C_4$-alkoxycarbonyl. If they are substituted, A and B are in particular in the form of the 1,3-propylene radical.

Preferred radicals R are those of the formulae $$-A_1-O-(B_1-O)_p-E_1 \quad (V)$$

$$-A_1-O-CO-F_1-O-(B_1-O)_p-E_1 \quad (VI)$$

and $$-A_1-(O-F_1)_{p1}-CO-O-(B_1-O)_p-E_1 \quad (VII)$$

wherein
$A_1$ represents a direct bond, 1,2-ethylene or 1,3-propylene which is optionally substituted by chlorine, hydroxyl or acetoxy,
$B_1$ represents 1,2-ethylene or 1,3-propylene which is optionally substituted by chlorine, hydroxyl or acetoxy,
$E_1$ represents hydrogen, $C_1$-$C_4$-alkyl, phenyl, $C_1$-$C_4$-alkylcarbonyl, formyl or benzoyl,
$F_1$ represents $C_1$- or $C_2$-alkylene,
p represents 1 to 3 and
$p_1$ represents 0 or 1.

The radical of the formulae (II) or (V) are particularly preferred.

Amongst these radicals, those in which E or $E_1$ represents a $C_1$-$C_4$-alkyl or phenyl radical and wherein p represents 1 or 2 when A or $A_1$ denotes a direct bond, or p represents 1 when A or $A_1$ denotes alkylene are to be mentioned in particular.

D represents the radical of an aromatic-carbocyclic or aromatic-heterocyclic diazo component, especially a radical of the benzene, thiazole, benzthiazole, benzisothiazole, thiadiazole, pyrazole, indazole, imidazole, benzimidazole, triazole, benztriazole, pyridine, pyrazolopyridine, quinoline or benzoxazole series.

K represents the radical of an aromatic-carbocyclic or aromatic-heterocyclic coupling component, above all the radical of a coupling component of the benzene, naphthalene, indole, dihydroindole, pyrazole, pyrazolone, indazole, imidazole, benzimidazole, benztriazole, benzisothiazole, benzthiazole, tetrahydroquinoline, acetoacetic acid ester, acetoacetic acid amide, cyanoacetic acid ester, cyanoacetic acid amide or malonodinitrile series.

The radicals of diazo components of the aromatic-carbocyclic series are understood as, preferably, the radicals of the formula

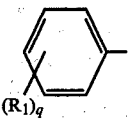

wherein
q represents 1 to 5 and
$R_1$ represents identical or different radicals and represents $C_1$-$C_4$-alkyl which is optionally substituted by halogen, or nitro, $C_1$-$C_4$-alkoxy, $C_1$-$C_3$-alkylcarbonylamino or -sulphonylamino, halogen, cyano, $C_1$-$C_4$-alkylsulphonyl, or aminocarbonyl or aminosulphonyl which are optionally substituted by $C_1$-$C_4$-alkyl, or phenyl, benzyl or benzoyl or represents R, or
one of the radicals $R_1$ represents

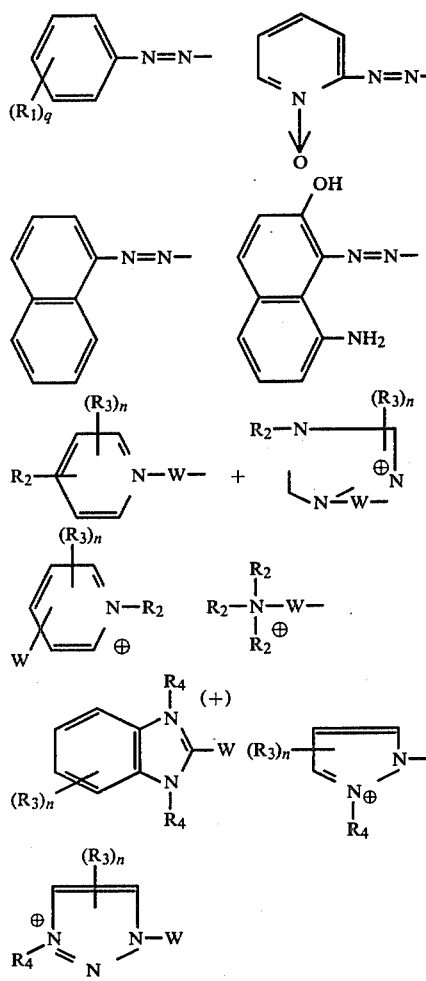

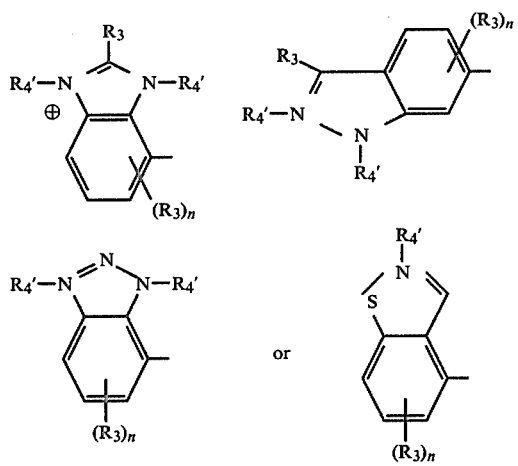

wherein

W represents $C_2$–$C_4$-alkylene, —$CH_2$—CO—, —$C_2H_4$—CO—, —$CH_2$—CONH—, —$C_2H_4$—O—, —$C_2H_4$—CONH—, —$C_2H_4$—O—CO—, —$C_3H_6$—OCO—, —$C_3H_6$—NHCO—, —S—, —$C_2H_4$—$NHSO_2$—, —$C_3H_6$—$NHSO_2$—, —$C_2H_4$—O—$C_2H_4$—, —$CH_2$—CO—$CH_2$—, —NH—, —N($C_1$–$C_4$—alkyl)—, or a direct bond, $R_2$ represents identical or different radicals and denotes hydrogen, R, $C_1$–$C_6$-alkyl or $C_2$–$C_6$-alkenyl which are optionally substituted by halogen, cyano, aminocarbonyl, hydroxyl, $C_1$–$C_4$-alkoxy, $C_1$–$C_3$-alkoxycarbonyl, $C_1$–$C_3$-alkylcarbonyloxy or phenoxy, or benzyl or phenylethyl which are optionally substituted by halogen, $C_1$–$C_4$-alkoxy, $C_1$–$C_4$-alkyl or R, it being possible for two radicals $R_2$ conjointly also to denote tetramethylene, pentamethylene or 3-aza- or 3-oxapentamethylene and it being possible for one radical $R_2$ also to denote $N(R_2)_2$, $R_3$ denotes identical or different radicals and represents R, hydrogen, $C_1$–$C_4$-alkyl, $C_1$–$C_4$-alkoxy, $C_1$–$C_3$-alkylcarbonylamino, $C_1$–$C_3$-alkylsulphonylamino, or phenyl or phenoxy which are optionally substituted by R, $C_1$–$C_4$-alkyl or $C_1$–$C_4$-alkoxy, or nitro, cyano, halogen, aminocarbonyl, aminosulphonyl, benzoyl, $C_1$–$C_3$-alkylcarbonyl or $C_1$–$C_3$-alkylsulphonyl and $R_4$ represent identical or different radicals and denotes hydrogen, R, $C_1$–$C_4$-alkyl or $C_3$–$C_4$-alkenyl which are optionally substituted by halogen, cyano, aminocarbonyl, hydroxyl, $C_1$–$C_4$-alkoxy, $C_1$–$C_3$-alkoxycarbonyl, $C_1$–$C_3$-alkylcarbonyloxy or phenoxy, or benzyl or phenylethyl which are optionally substituted by halogen, $C_1$–$C_4$-alkyl, $C_1$–$C_4$-alkoxy or R, and n represents 1 or 2, with the proviso that A preferably represents alkylene when $R_2$ and $R_4$ represent the radical II and that A represents alkylene when $R_2$ or $R_4$ represent the radicals III or IV.

A radical of a diazo component of the aromatic-heterocyclic series is understood as, preferably, the following radicals:

1. Radicals which are bonded to the azo bridge via a fused benzene ring and having the formulae wherein $R_4'$ represents R or $C_1$–$C_4$-alkyl or $C_3$–$C_4$-alkenyl which are optionally substituted by halogen, cyano, aminocarbonyl, hydroxyl, $C_1$–$C_4$-alkoxy, $C_1$–$C_3$-alkoxycarbonyl, $C_1$–$C_3$-alkylcarbonyloxy or phenoxy, or benzyl or phenylethyl which are optionally substituted by halogen, $C_1$–$C_4$-alkyl or $C_1$–$C_4$-alkoxy.

2. Radicals which are free from quaternary ring nitrogen atoms and have the formulae

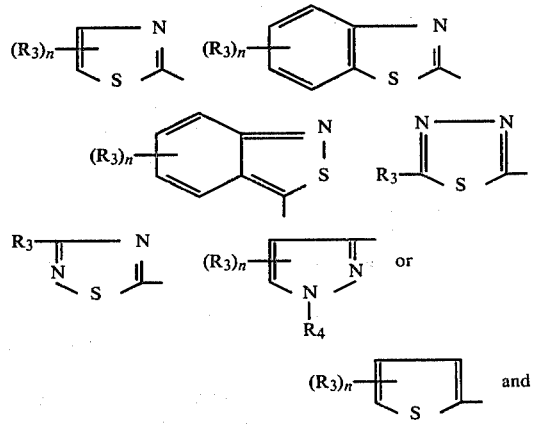

3. Radicals which contain a quaternary ring nitrogen atom and having the formulae

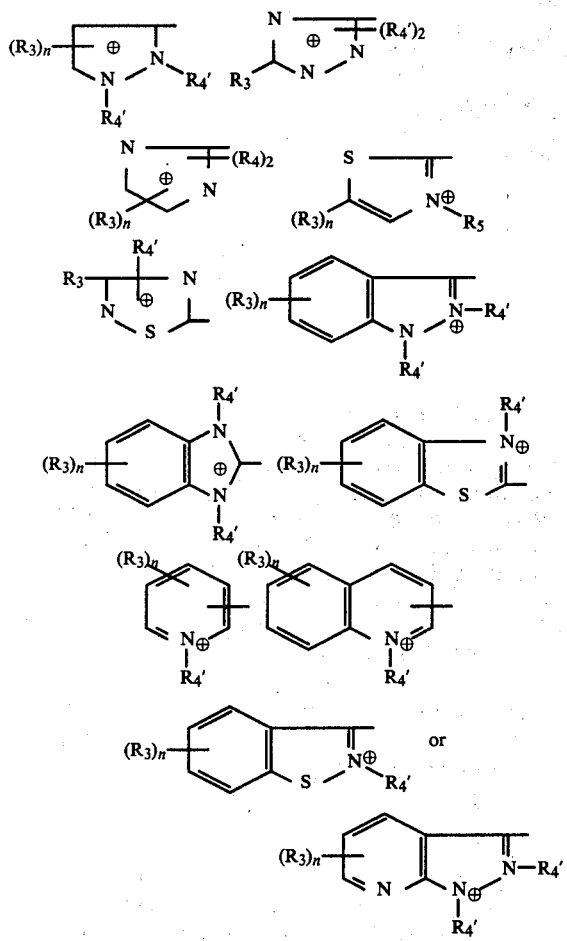

A radical of a coupling component of the aromatic-carbocyclic series is understood as, preferably, radicals of the formulae

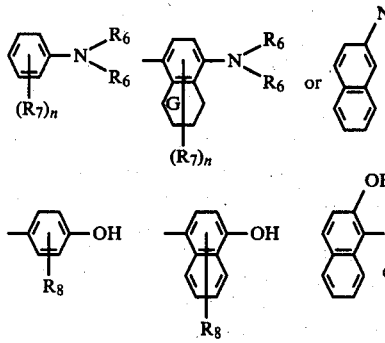

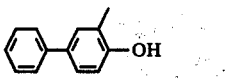

wherein $R_6$ has the same meaning as $R_2$ or represents a radical of the formula

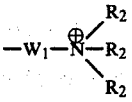

wherein
- $W_1$ represents a direct bond or a straight-chain or branched $C_2$–$C_5$-alkylene radical and
- $R_7$ represents R, hydrogen, $C_1$–$C_5$-alkyl, $C_1$–$C_4$-alkoxy, phenoxy, benzyloxy, halogen, $C_1$–$C_3$-alkyl-carbonylamino or -sulphonylamino, $C_1$–$C_3$-alkoxycarbonylamino or benzoyl- or phenyl-sulphonylamino,
- $R_2$ and $R_6$, conjointly with $W_1$ and the nitrogen atoms to which they are bonded, can form a piperazine ring, the ring G, conjointly with the fused benzene ring, forms a naphthalene or tetrahydronaphthalene ring, $R_2$ and n have the abovementioned meaning and
- $R_8$ represents R, hydrogen, halogen, $C_1$–$C_4$-alkyl, p-aminophenylazo or amino which is optionally substituted by $C_1$–$C_4$-alkyl.

A radical of a coupling component of the aromatic-heterocyclic series is understood as, preferably, the following radicals:

1. Radicals which are bonded to the azo bridge via a fused benzene ring and have the formulae

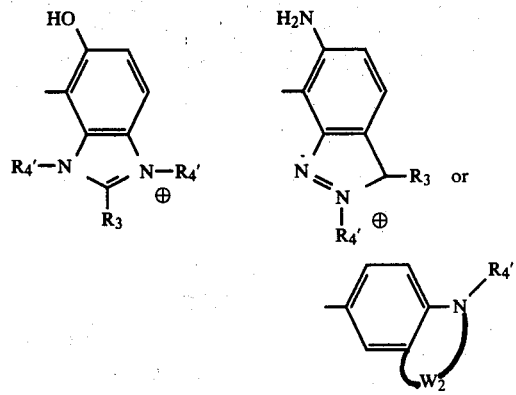

wherein
- $W_2$ denotes ethylene or propylene which are optionally substituted by $C_1$–$C_4$-alkyl and
- $R_3$ and $R_4'$ have the abovementioned meaning, and 2. Radicals which are bonded to the azo bridge via a heterocyclic ring and have the formulae

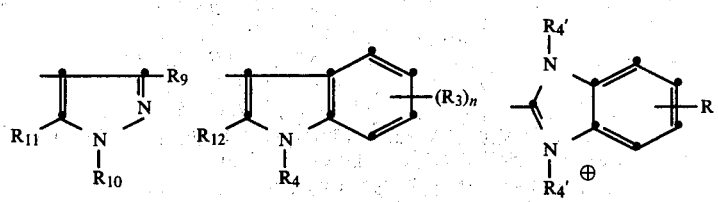

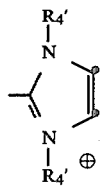 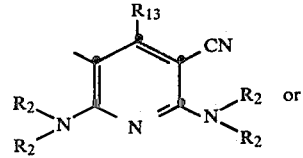 or 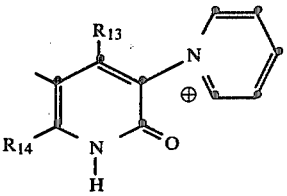

wherein
$R_9$ represents $C_1$-$C_4$-alkyl, $C_1$-$C_3$-alkoxycarbonyl, aminocarbonyl or R,
$R_{10}$ represents $R_2$, phenyl which is optionally substituted by halogen or $C_1$-$C_4$-alkyl, or R,
$R_{11}$ represents OH or $NH_2$,
$R_{12}$ represents $C_1$-$C_4$-alkyl or phenyl,
$R_{13}$ represents $C_1$-$C_4$-alkyl and
$R_{14}$ represents hydroxyl or $N(R_2)_2$ and
$R_2$, $R_3$ and $R_4$ have the abovementioned meaning.

Preferred dyestuffs are those of the formula

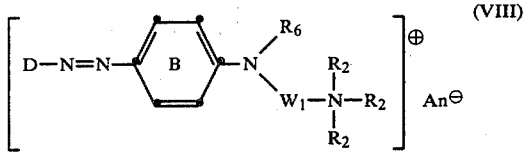 (VIII)

wherein
D denotes the radical of a diazo component of the benzene, benzthiazole, benzisothiazole, 1,3,4-thiadiazole-(2), 1,2,4-thiadiazole-(5), 1,3-thiazole-(2), pyridine-(2) or pyridine-(4) series and
$W_1$ denotes a straight-chain or branched $C_2$-$C_5$-alkylene radical,
$R_6$ denotes hydrogen, R, a $C_1$-$C_6$-alkyl radical, which can be substituted by chlorine, bromine, cyano, hydroxyl, $C_1$-$C_4$-alkoxy, $C_1$-$C_4$-alkoxycarbonyl or $C_1$-$C_4$-alkylcarbonyloxy, or a $C_3$- or $C_4$-alkenyl radical or a radical of the formula

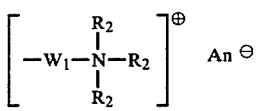

$R_2$ has the abovementioned meaning or
$R_6'$, conjointly with N—$W_1$—N—R is a piperazine ring
and wherein
the ring B can be substituted by R, $C_1$-$C_5$-alkyl, $C_1$-$C_4$-alkoxy, halogen, phenoxy, benzyloxy, $C_1$-$C_3$-alkylcarbonylamino or -sulphonylamino, $C_1$-$C_3$-alkoxycarbonylamino, benzoylsulphonylamino or phenylsulphonylamino and
An$^\ominus$ denotes an anion,
and wherein
at least one radical R is present.

Dyestuffs of the formula VIII wherein D represents a phenyl radical which can be substituted by 1 to 4 of the following radicals: $C_1$-$C_4$-alkyl, cyclohexyl, phenyl which is optionally substituted by $C_1$-$C_4$-alkyl, cyano, chlorine, bromine, nitro or $C_1$-$C_4$-alkoxy, $C_1$-$C_4$-alkoxy, benzyloxy, phenoxy, fluorine, chlorine, bromine, iodine, cyano, nitro, $C_1$-$C_4$-alkylcarbonyl, benzoyl, $C_1$-$C_4$-alkylsulphonyl, phenylsulphonyl, p-toluylsulphonyl, fluoromethyl, difluoromethyl, trifluoromethyl, trichloromethyl, $C_1$-$C_4$-alkoxycarbonyl, aminocarbonyl, aminosulphonyl which is optionally substituted by methyl, or $C_1$-$C_4$-alkylcarbonyloxy, $C_1$-$C_4$-alkyl-carbonylamino or -sulphonylamino, benzoylamino, phenylsulphonylamino, phenylazo, naphthylazo or R, or represents radicals of the formulae

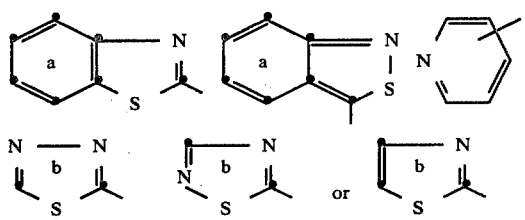

in which a nitrogen atom can be quaternised by $R_2$ and in which the rings a can be substituted by $C_1$-$C_4$-alkyl, $C_1$-$C_4$-alkoxy, chlorine, bromine, nitro, cyano, $C_1$-$C_4$-alkyl-carbonyl or -sulphonyll, $C_1$-$C_4$-alkoxycarbonyl, amino-carbonyl or -sulphonyl, $C_1$-$C_4$-alkylcarbonyloxy, $C_1$-$C_4$-alkyl-carbonylamino or -sulphonylamino or R and the rings b can be substituted by nitro, cyano, $C_1$-$C_6$-alkyl, cyclohexyl, phenyl which is optionally substituted by $C_1$-$C_4$-alkyl, $C_1$-$C_4$-alkoxy, chlorine, nitro, $C_1$-$C_4$-alkoxycarbonyl, $C_1$-$C_4$-alkylamino, acetylamino, phenoxy or acetyl, or benzyl, $C_1$-$C_4$-alkoxy, phenoxy, cyclohexyloxy, $C_1$-$C_4$-alkoxycarbonyl, $C_1$-$C_{12}$-alkylmercapto, phenylmercapto, benzylmercapto, $C_1$-$C_4$-alkylsulphonyl, benzylsulphonyl, di-$C_1$-$C_4$-alkylamino, pyrrolidino, piperidino, dibenzylamino, diphenylamino, benzyloxy, furyl or R, are particularly worthy of mention.

Amongst the dyestuffs VIII, those in which the radical R is bonded to the quaternary nitrogen atom and represents the preferred radicals V to VII are also to be singled out.

Particularly preferred dyestuffs of the formula VIII are those of the formula

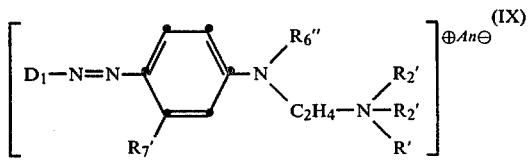 (IX)

in which $D_1$ represents radicals of the formulae

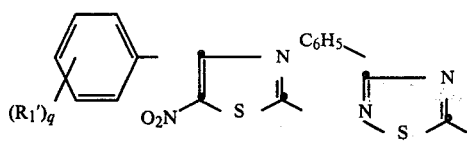

wherein
R$_1'$ are identical or different and represent methyl, cyano, nitro, methylsulphonyl, chlorine or bromine,
q represents 0, 1, 2 or 3,
R$_2'$ represents methyl, ethyl, allyl or methallyl,
R$_6''$ represents methyl or ethyl,
R$_7'$ represents hydrogen or methyl,
R' represents

—A$_1$—O—B$_1$—O—E$_2$

—A$_1$—O—CO—F$_1$—O—B$_1$—O—E$_2$ or

—A$_1$—COO—B$_1$—O—E$_2$ in which
E$_2$=C$_1$-C$_4$-alkyl, or represents phenyl and
An$^\ominus$ represents an anion.

Further preferred dyestuffs of the formula I are dyestuffs of the formula

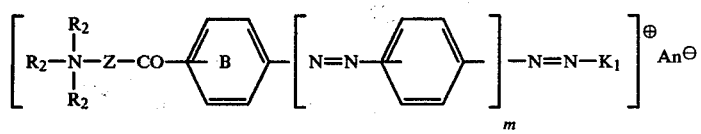

wherein
R$_2$ and An$^\ominus$ have the abovementioned meaning,
Z represents a C$_1$-C$_3$-alkylene radical,
K$_1$ represents a coupling component of the benzene, naphthalene, indole, pyrazolone or aminopyrazole series and
m represents 0 or 1,
and wherein
ring B can be substituted by 1 or 2 of the following radicals: C$_1$-C$_4$-alkyl, C$_1$-C$_4$-alkoxy, C$_1$-C$_4$-alkylsulphonyl, halogen, cyano, nitro or R,
and wherein
at least one radical R is present.

Amongst these dyestuffs, in turn, those in which K$_1$ represents the following radicals:

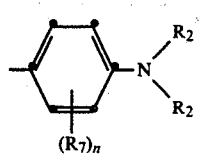

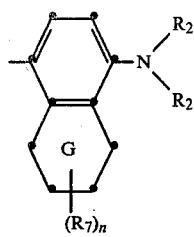

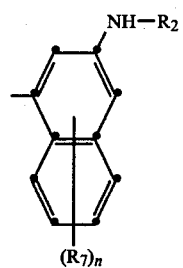

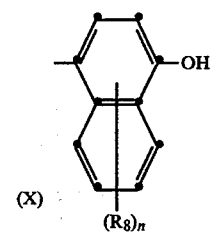

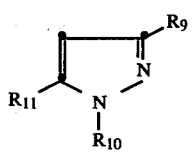

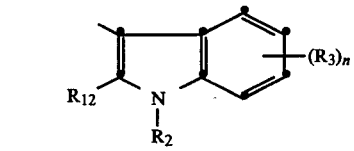

are to be mentioned.

In these radicals, R$_2$, R$_3$, R$_7$ to R$_{12}$ and n have the abovementioned meaning.

Amongst the dyestuffs X, those in which the radical R is bonded to the quaternary nitrogen atom and represents the preferred radicals V to VII are to be singled out.

Particularly preferred dyestuffs of the formula X are dyestuffs of the formula

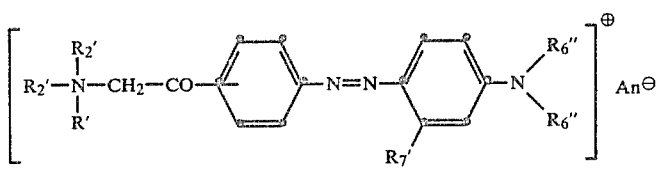

in which
R$_2'$ represents methyl, ethyl, allyl or methallyl,
R$_6''$ represents hydrogen, methyl, ethyl, cyanoethyl or allyl,
R$_7'$ represents hydrogen, methyl or chlorine,
R' represents

—A$_1$—O—B$_1$—O—E$_2$

—A$_1$—O—CO—F$_1$—O—B$_1$—O—E$_2$ or

—A$_1$—COO—B$_1$—O—E$_2$ in which
E$_2$=C$_1$–C$_4$-alkyl, or represents phenyl and
An$^\ominus$ represents an anion.
Dyestuffs of the formula

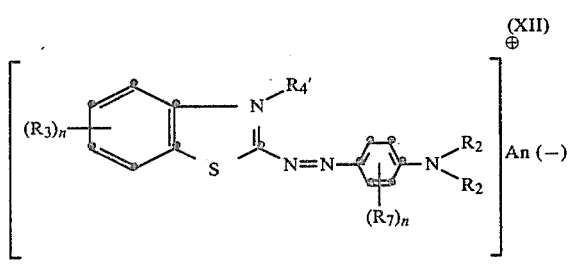

wherein
the symbols have the abovementioned meaning
and wherein
at least one radical R is present,
are also preferred dyestuffs of the formula I.
Amongst the dyestuffs XII, the dyestuffs of the formula

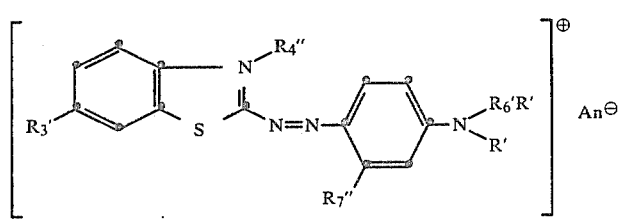

wherein
R$_3'$ denotes hydrogen, methoxy, ethoxy or acetylamino,
R$_4''$ denotes methyl or ethyl,
R$_6'''$ denotes methyl, ethyl, cyanoethyl or allyl,
R$_7''$ denotes hydrogen or methyl and
R' and An$^\ominus$ have the abovementioned meaning,
are preferred.
Dyestuffs of the formula

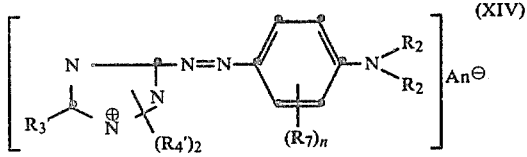

wherein
R$_2$, R$_3$, R$_7$, n and An$^\ominus$ have the abovementioned meaning and
R$_4'$ represents R or C$_1$–C$_4$-alkyl or C$_3$–C$_4$-alkenyl which are optionally substituted by halogen, cyano, aminocarbonyl, hydroxyl, C$_1$–C$_4$-alkoxy, C$_1$–C$_3$-alkoxycarbonyl, C$_1$–C$_3$-alkylcarbonyloxy or phenoxy, or benzyl or phenylethyl which are optionally substituted by halogen, C$_1$–C$_4$-alkyl or C$_1$–C$_4$-alkoxy,
and wherein
at least one radical R is present,
are also preferred dyestuffs of the formula I.
Amongst the dyestuffs XIV the dyestuffs of the formula

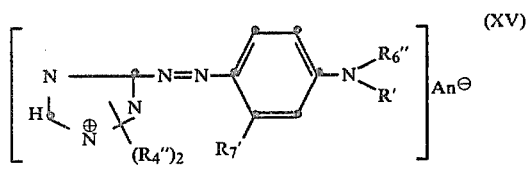

wherein
R', R$_4''$, R$_6''$, R$_7'$ and An$^-$ have the abovementioned meaning,
are preferred.

Dyestuffs of the formula

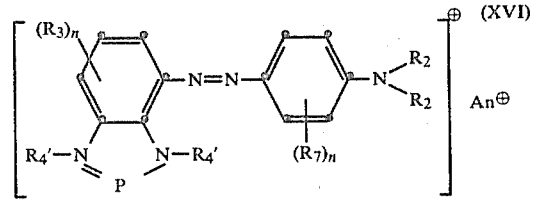

wherein $R_2$, $R_3$, $R_4'$, $R_7$, n and $An^\ominus$ have the abovementioned meaning, and P represents N or C—Q, in which Q = hydrogen, $C_1$-$C_4$-alkyl or phenyl, and wherein at least one radical R is present, are also preferred dyestuffs of the formula I.

Amongst the dyestuffs XVI, dyestuffs of the formula

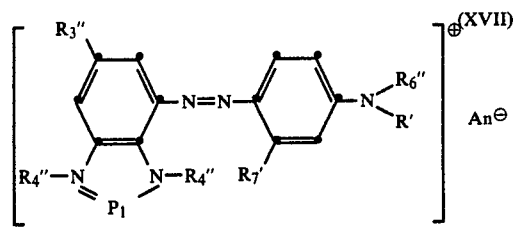 (XVII)

wherein $P_1$ denotes N or CH and $R_3''$ denotes hydrogen, methyl, trifluoromethyl, methoxy or chlorine and the other symbols have the abovementioned meaning, are preferred.

Dyestuffs of the formula

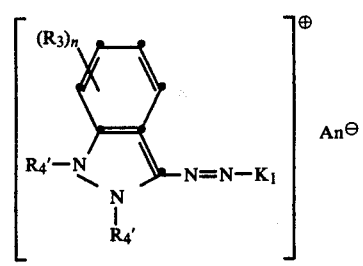 (XVIII)

wherein the symbols have the abovementioned meaning, and wherein at least radical R is present, are also preferred dyestuffs of the formula I.

Amongst the dyestuffs XVIII, dyestuffs of the formula

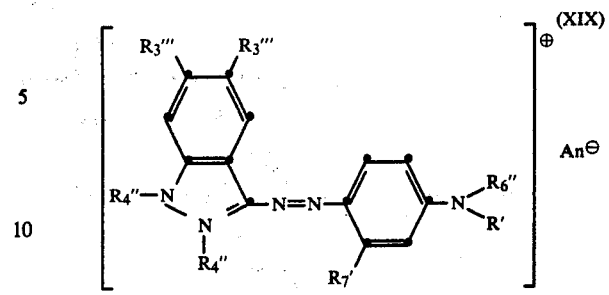 (XIX)

wherein $R_3'''$ denotes hydrogen, methyl, methoxy or nitro and the other symbols have the above meaning, are preferred.

The invention also relates to processes for the preparation of dyestuffs of the formula I by known methods customary in dyestuff chemistry.

The dyestuffs I can be prepared by reacting compounds of the formula $$R\text{—}X \qquad (XX)$$

wherein

R has the abovementioned meaning and

X represents a radical which is split off from R under the reaction conditions, with dyestuffs of the formula $$[D\text{—}N\text{=}N\text{—}K]^{m\oplus} mAn^\ominus \qquad (XXI)$$

or their non-quaternised precursors of the formula $$D\text{—}N\text{=}N\text{—}K \qquad (XXII)$$

or their optionally quaternised precursors of the formulae $$D\text{—}NH_2 \qquad (XXIII)$$

or $$HK \qquad (XXIV)$$

and where appropriate by subsequent quaternisation and/or diazotisation and coupling.

The radical R can be introduced into the compounds XXI to XXIV by three different routes.

Possibilities for linking and building up the radicals R:

1 (a)

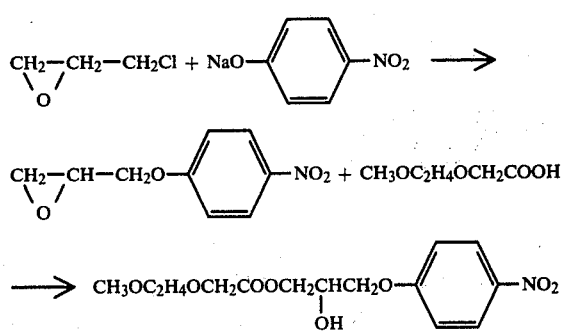

-continued
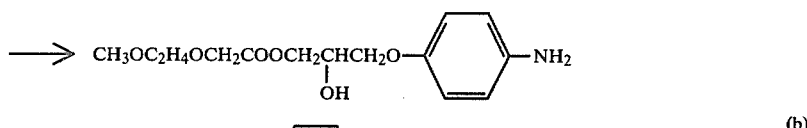
(b)
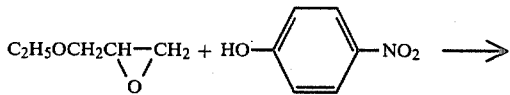
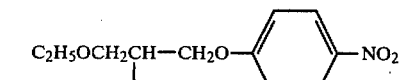
 
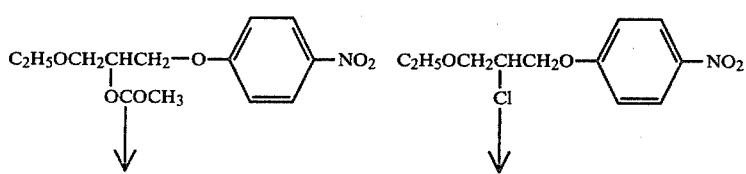
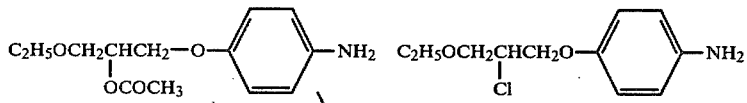
(c)
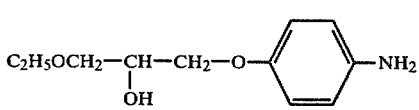
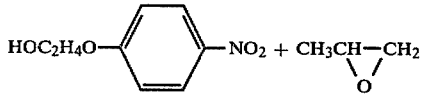
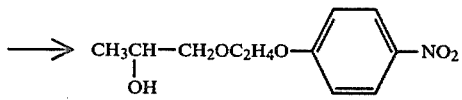
(d)
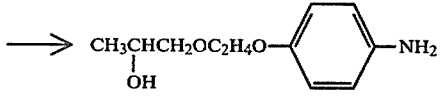
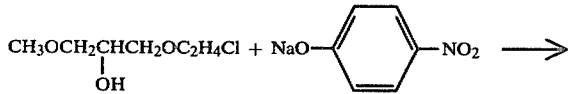
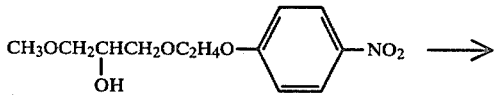
2 (a)
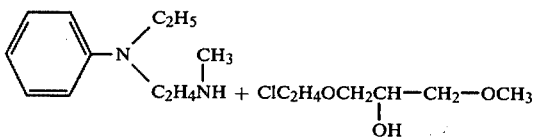

-continued
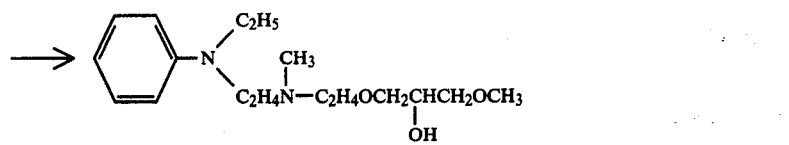
(b)
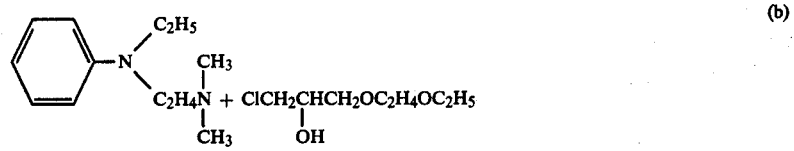
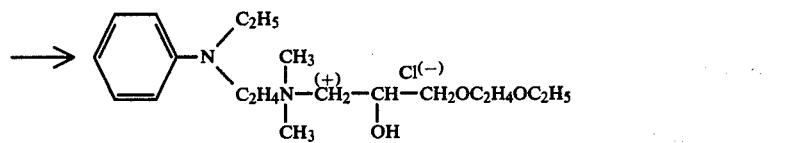
(d)
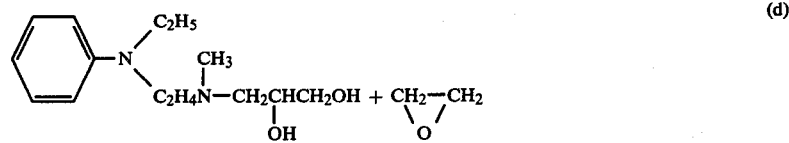
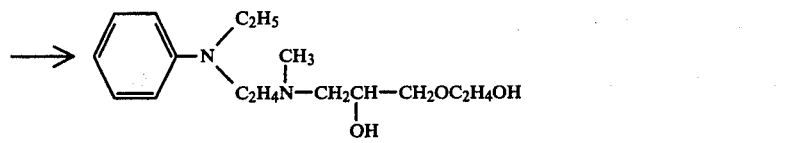
(e)
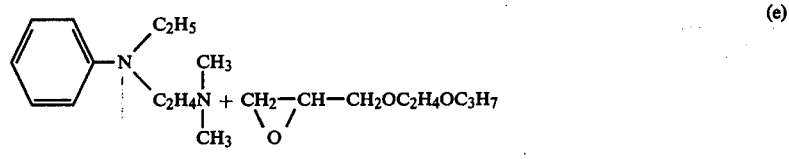
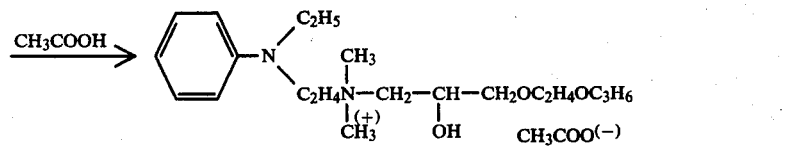
(f)
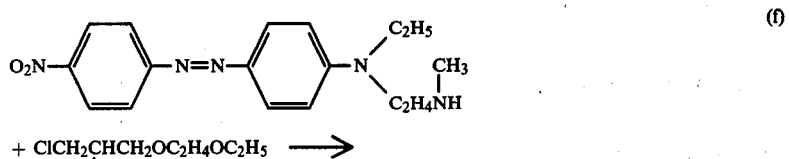
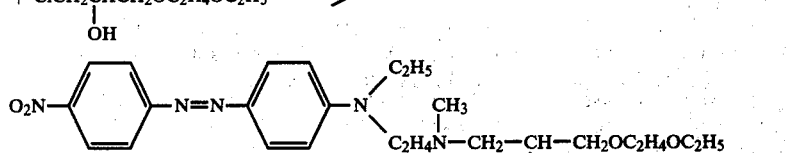
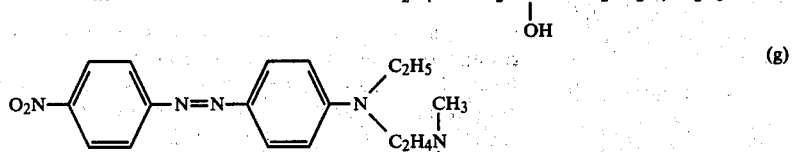
(g)
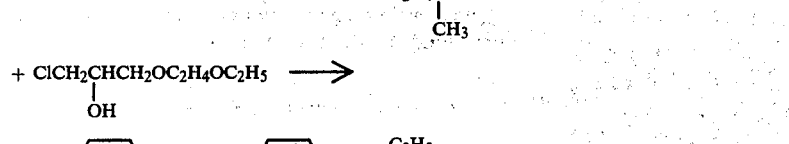
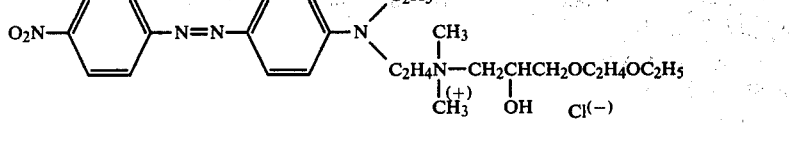

3 (a)

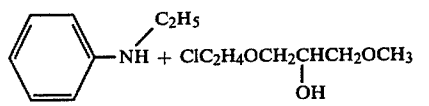

(b)

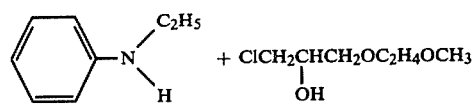

(c)

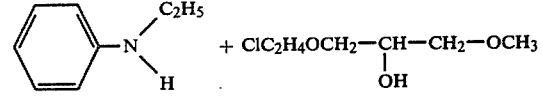

(d)

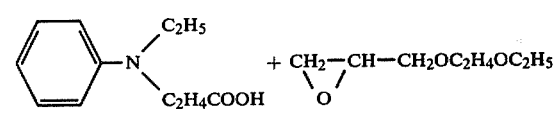

Diazo components of the formula XXIII are described, for example, in German Auslegeschriften (German Published Specifications) Nos. 1,098,642 and 1,644,243, German Offenlegungsschrift (German Published Specification) No. 2,057,977, U.S. Pat. Nos. 2,883,373, 3,051,697, 3,101,988, 3,332,930, 3,410,840 and 3,597,412, British Patent Specifications Nos. 1,117,588, 1,125,683, 1,134,175 and 1,342,380, Belgian Patent Specification No. 608,362 and French Patent Specifications Nos. 1,484,099 and 1,505,141.

Coupling components of the formula XXIV are described not only in the abovementioned patent specifications but also, for example, in German Auslegeschriften (German Published Specifications) Nos. 1,243,299, 1,297,255, 1,544,593, 2,054,697, 2,107,798, 2,209,208 and 2,209,209, U.S. Pat. No. 3,344,133, French Patent Specification No. 1,211,449 and Belgian Patent Specifications Nos. 548,936 and 706,104.

The quaternisation of the dyestuffs XXII, of the diazo component XXIII, of the coupling component XXIV or of the dyestuffs of the formula

is carried out in accordance with known methods in organic or aqueous solution or suspension at 5°–100° C. Examples of suitable organic solvents are chlorobenzene, toluene, carbon tetrachloride, dimethylformamide, N-methylpyrrolidone or glacial acetic acid.

Quaternising agents which may be mentioned are compounds of the formulae

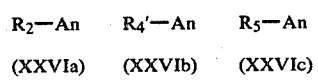

wherein An is to be understood as a radical which eliminates an anion $An^\ominus$ under the reaction conditions.

Examples of suitable quaternising compounds of this nature are alkyl halides, alkenyl halides, aralkyl halides, cycloalkyl halides, dialkyl sulphates, alkyl esters of arylsulphonic acids and other esters of strong mineral acids and organic sulphonic acids with, preferably, lower alkohols. The quaternising agents may be substituted further.

Examples are dimethyl sulphate, diethyl sulphate, methyl chloride, methyl bromide, methyl iodide, methyl sulphate, ethyl bromide, ethyl chloride, n-propyl bromide, n-butyl bromide, allyl chloride, methallyl chloride, 2-chlorodiethyl ether, chloroacetic acid and bromoacetic acid methyl ester, methanesulphonic acid methyl, ethyl and propyl ester, ethylene chlorohydrin,, δ-chloropropionic acid methyl ester, chloroacetonitrile, acetic acid β-chloroethyl ester, benzyl chloride, phenylethyl chloride, phenoxy-β-chloroethyl, butenyl chloride, chloramine, O-methylsulphonylhydroxylamine, O-mesitylenesulphonylhydroxylamine, N,N-dimethylchloramine, hydroxylamine-O-sulphonic acid and also hydrochloric acid, sulphuric acid, methylsulphonic acid, phosphoric acid, formic acid, acetic acid, propionic acid, lactic acid and β-hydroxypropionic acid.

The quaternising agents of the formula XXVIa and XXVIb also include the compounds of the formula $$R-X \qquad (XX)$$

in which
R represents a radical II–IV,
in which
A denotes an alkylene radical, and
X represents halogen or a $C_1$–$C_4$-alkyl-, phenyl- or tolyl-sulphonyloxy radical.

Examples of these compounds are:

$$CH_3-SO_3-(C_2H_4-O)_2-CO-CH_3$$
$$Br-(C_2H_4-O)_3-C_2H_4-OH$$
$$Br-C_2H_4-O-CH_2\underset{OH}{CH}-CH_2-O-CH_3$$
$$Cl-CH_2-\underset{OH}{CH}-CH_2O-(C_2H_4-O)_2-CH_3$$
$$Cl-CH_2-\underset{OH}{CH}CH_2-O-CO-CH_2-(C_2H_4-O)_2-CH_3$$
$$Br-C_2H_4-O-CH_2-CO-O-CH_2-\underset{OH}{CH}-CH_2-O-C_2H_4-O-CH_3$$

The compounds XXVIa or XXVIb are also to be understood to include those which in the presence of an acid H-An form the radicals $R_2$, $R_4$ and $R_5$, respectively, with elimination of the anion $An^\ominus$. Examples are acrylic acid and its derivatives, such as acrylonitrile or acrylamide, alkylene oxides, such as ethylene oxide, and vinylpyridines such as 2-vinylpyridine.

Possible anionic radicals $An^\ominus$ are the organic and inorganic anions customary for cationic dyestuffs.

The anion is in general decided by the process of preparation and by any purification of the crude dyestuff which may be carried out. However, the anions can also be exchanged in a known manner for other anions. In general, the dyestuffs are in the form of halides (especially as chlorides, bromides or iodides) or as methosulphates, ethosulphates, sulphates, phosphates, methylsulphonates, benzenesulphonates or toluenesulphonates, formates, acetates, propionates or hydroxypropionates. Colourless anions are preferred.

The following may be mentioned as preferred embodiments of the preparation of the dyestuffs I:

Preparation of dyestuffs VIII by reacting compounds of the formula

<pre>
        R6'
         |
    B—N
         \
          W1—N—R2
              |
              R2
</pre>
(XXVII)

with amines of the formula $$D-NH_2 \qquad (XXVIII)$$

after diazotisation of the latter, and with quaternising agents of the formula XXVIa, in optional sequence.

Preparation of dyestuffs X by reacting compounds of the formula (XXIX)

$$R_2{\diagdown}N-Z-CO-B-[N=N-\phantom{xx}]_m-NH-Z_1$$

wherein $Z_1$ denotes hydrogen or acetyl, after diazotisation, with compounds of the formula $$H-K_1$$

and with quaternising agents XXVIa, in optional sequence.

Preparation of dyestuffs XII by reacting dyestuffs of the formula (XXX)

with the quaternising agents of the formula XXVIc.

Preparation of dyestuffs XIV by reacting dyestuffs of the formula

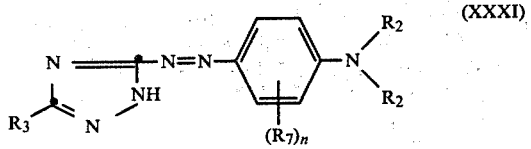

with the quaternising agents of the formula XXVIb.

Preparation of dyestuffs XVI by reacting dyestuffs of the formula

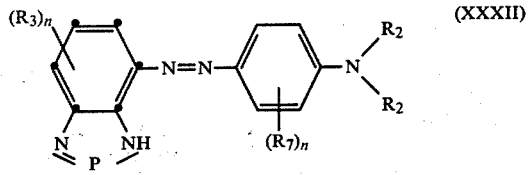

with the quaternising agents of the formula XXVIb.

Preparation of dyestuffs XVIII by reacting dyestuffs of the formula

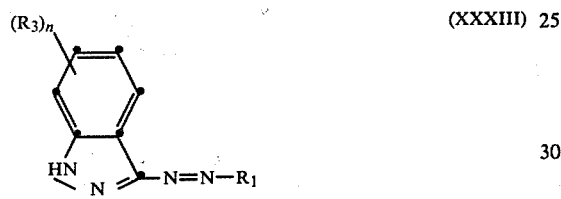

with the quaternising agents of the formula XXVIb.

The new dyestuffs can be used for dyeing, printing and bulk dyeing of materials containing acid groups, above all of products which consist entirely or predominantly of polymerised unsaturated nitriles, such as acrylonitrile and vinylidene cyanide, or of acid-modified polyesters or of acid-modified polyamides. The fibres are described, for example in U.S. Pat. Nos. 3,018,272, 3,166,531, 3,039,990 and 3,454,351. The can furthermore be used for the other known uses of cationic dyestuffs, such as dyeing and printing cellulose acetate, tannin-treated cotton and paper, for the preparation of pastes for ballpoint pens, and inks for rubber stamps, and for use in flexographic printing.

The new dyestuffs can be used with particular advantage for dyeing polyacrylonitrile filaments which are obtained in accordance with the wet spinning process.

Dyeing will be carried out in a known manner, from a neutral or weakly acid liquor, at 40°–100° C. or under pressure at above 100° C. It can be carried out with the addition of customary auxiliaries, for example in the presence of retarders or emulsifiers.

When the dyestuffs are used for printing the stated polymers, customary auxiliaries, such as wetting agents and thickeners, are added to the printing inks.

The new dyestuffs exhibit a surprisingly good solubility in water. This permits the preparation of storage-stable, concentrated solutions, which are free from organic solvents and can be marketed, and employed in dyeing and printing processes, in place of dyestuff powders and the hitherto almost exclusively solvent-containing liquid types. It proves possible to prepare storage-stable concentrated solutions containing, for example, 20–70% of dyestuff. The use of these dyestuff solutions instead of dyestuff powders is advantageous because this avoids the objectionable introduction of organic solvents, and of the extenders usually present in the powders, such as dextrin or salts, into dyeing liquors and effluents.

The rate of absorption of the new dyestuffs is not affected adversely in relation to comparable dyestuffs which are substituted by hydrogen or an alkyl group in place of the radical R.

The dyestuffs possess good fastness properties, such as fastness to light and to wet processing, high affinity to the fibre, good migrating capacity and substantial insensitivity to thiocyanate ions which, in the case of industrially important dyeing processes, are frequently carried into the dye baths due to the nature of the process.

EXAMPLE 1

17.25 parts by weight of 2-chloro-4-nitraniline are stirred with 30 parts by weight of water and 50 parts by weight of 30% strength hydrochloric acid for 10 hours to form a paste, and are then diazotised, at 0° to 5° C., with a solution of 7 g of sodium nitrate and 25 cm³ of water. The solution is clarified and combined with a solution of 30.8 parts by weight of the amine

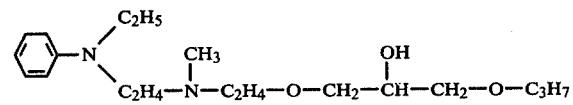

in dilute acetic acid, and the mixture is rendered alkaline by slow dropwise addition of sodium hydroxide solution, whilst stirring. The dyestuff which has separated out is filtered off, washed free from salt, or freed from salt by repeated decanting with water, and rendered neutral to weakly acid with dilute acetic acid. A 50% strength aqueous solution of this red dyestuff is stable for months even at 0° C.

If the molar amount of dimethyl sulphate is added whilst stirring at 20° to 40° C., a solution of the dyestuff of the formula

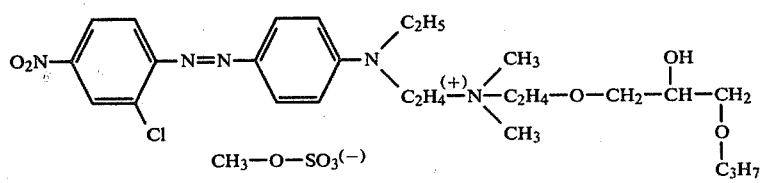

of the same colour is obtained. Here again, a 50% strength aqueous solution is stable. The solubility of the corresponding trimethylammonium dyestuff in water is about 1 g/liter at room temperature.

EXAMPLE 2

35.5 g of dyestuffs of the formula

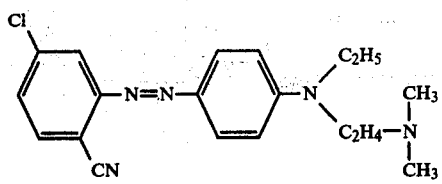

27 g of water and 0.5 g of sodium carbonate are stirred at 80° C. and 20.5 g of substance of the formula

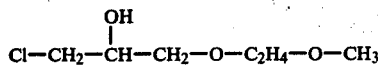

are added dropwise in the course of one hour, after which the mixture is stirred for about 15 hours at 80° to 90° C. A mobile red dyestuff solution of the dyestuff of the formula

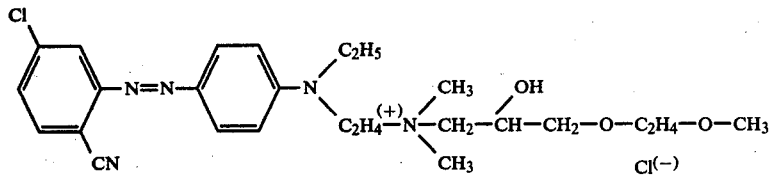

which can be diluted with water in all proportions is obtained.

EXAMPLE 3

The diazo solution from Example 1 is used and 32.7 g of the coupling base of the formula

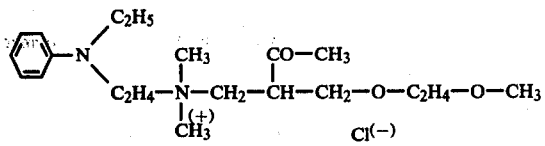

are added, and the mixture is neutralised to pH 7 with sodium hydroxide solution. On addition of sodium chloride, the dyestuff of the formula

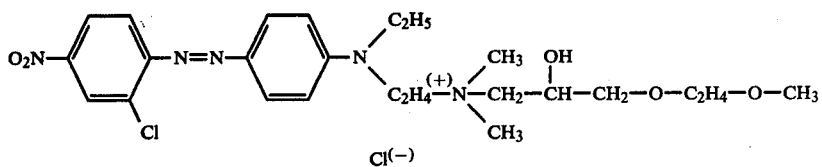

separates out as a viscous oil. The salt solution is completely decanted, and sufficient water is added to produce a 35% strength solution which is adjusted to pH 4 with a little glacial acetic acid. The solution is stable even at 0° C. If instead of sodium chloride concentrated sodium hydroxide solution is added at 0°–10° C., the oily dyestuff is separated from the aqueous solution and glacial acetic acid added until the pH is 4, a water-miscible dyestuff of lower viscosity, for the same dyestuff content, is obtained.

The coupling base can be obtained by boiling 24 g of the base

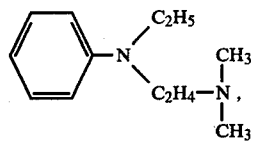

14 g of β-(δ-chloro-β-acetoxypropyl)-ethyl methyl ether and 50 cm³ of water for 8 to 10 hours and then saponifying the acetyl group.

The following dyestuffs, which dye polyacrylonitrile in the stated colour shade, are obtained in the same manner

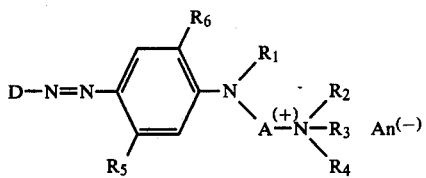

| No. | D | A | $R_1$ | $R_2$ | $R_3$ | $R_4$ | $R_5$ | $R_6$ | $An^{(-)}$ | Colour shade |
|---|---|---|---|---|---|---|---|---|---|---|
| 1 | 2-Chloro-4-nitrophenyl | $C_2H_4$ | $CH_2$—CH—$CH_2$— <br> \| <br> OH <br> O—$C_2H_4$—OH | $CH_3$ | $CH_3$ | $CH_3$ | H | H | $Cl^-$ | red |
| 2 | 2-Chloro-4-nitrophenyl | $C_3H_6$ | $CH_2$—CH—$CH_2$— <br> \| <br> OH <br> O—$C_2H_4$—OH | " | $CH_2$—CH=$CH_2$ | " | " | " | $HSO_4^-$ | " |

-continued

| No. | D | A | $R_1$ | $R_2$ | $R_3$ | $R_4$ | $R_5$ | $R_6$ | $An^{(-)}$ | Colour shade |
|---|---|---|---|---|---|---|---|---|---|---|
| 3 | 2-Chloro-4-nitrophenyl | $C_2H_4$ | $C_2H_5$ | " | $C_2H_4-O-CH_2-\underset{\underset{CH_2-O-\phi}{\mid}}{\overset{\overset{OH}{\mid}}{CH}}-$ | " | " | " | $Cl^-$ | " |
| 4 | 2-Chloro-4-nitrophenyl | $C_2H_4$ | $C_2H_4-O-CH_2-\underset{\underset{OH}{\mid}}{CH}-CH_2-O-CH_3$ | " | $CH_3$ | " | " | " | $Br^-$ | " |
| 5 | 2-Chloro-4-nitrophenyl | $C_2H_4$ | $CH_3$ | " | $C_2H_4-O-CH_2-\underset{\underset{-CH_2-O-C_2H_4-O-C_2H_5}{\mid}}{\overset{\overset{}{\mid}}{CH}}$ Cl | $CH_2-\phi$ | $CH_3$ | " | $Cl^-$ | " |
| 6 | 2-Cyano-4-nitro-phenyl | $C_2H_4$ | $C_2H_5$ | " | $CH_2-\underset{\underset{(C_2H_4-O)_2-C_4H_9}{\mid}}{\overset{\overset{OH}{\mid}}{CH}}-CH_2-O-$ | $CH_3$ | H | " | $Cl^-$ | " |
| 7 | 2-Cyano-4-nitro-phenyl | $C_2H_4$ | $C_2H_5$ | $CH_3$ | $CH_2-\underset{\underset{C_2H_4-O-C_4H_9}{\mid}}{\overset{\overset{OH}{\mid}}{CH}}-CH_2-O-$ | $CH_3$ | H | H | $Cl^-$ | red |
| 8 | 2-Cyano-4-nitro-phenyl | " | " | " | $C_2H_4-O-CH_2-\underset{\underset{O-CO-CH_3}{\mid}}{CH}-CH_2-O-CH_3$ | " | " | " | $Cl^-$ | red |
| 9 | 2-Cyano-4-nitro-phenyl | " | " | " | $C_2H_4-O-CH_2-\underset{\underset{-CH_2-O-C_2H_5}{\mid}}{\overset{\overset{Cl}{\mid}}{CH}}$ | " | " | " | $Cl^-$ | red |
| 10 | 2,4-Dicyano-phenyl | " | " | " | $CH_2-\underset{\underset{C_2H_4-O-C_4H_9}{\mid}}{\overset{\overset{OH}{\mid}}{CH}}-CH_2-O-$ | " | " | " | $Cl^-$ | red |
| 11 | 3,4-Dicyano-phenyl | " | " | " | $CH_2-\underset{\underset{C_2H_4-O-C_4H_9}{\mid}}{\overset{\overset{OH}{\mid}}{CH}}-CH_2-O-$ | " | $OCH_3$ | " | $Cl^-$ | orange |
| 12 | 3,4-Dicyano-phenyl | $C_2H_4$ | $C_2H_5$ | $CH_3$ | $CH_2-\underset{\underset{C_2H_4-O-C_4H_9}{\mid}}{\overset{\overset{OH}{\mid}}{CH}}-CH_2-O-$ | $CH_3$ | $OCH_3$ | $OCH_3$ | $Cl^-$ | orange |
| 13 | 2-Cyano-5-chloro-phenyl | " | " | " | $C_2H_4-O-CH_2-\underset{\underset{-CH_2-O-C_4H_9}{\mid}}{\overset{\overset{OH}{\mid}}{CH}}$ | " | H | H | $Cl^-$ | " |
| 14 | 2,6-Di-chloro-4-nitrophenyl | " | " | " | $C_2H_4-O-CH_2-\underset{\underset{-CH_2-O-C_4H_9}{\mid}}{\overset{\overset{OH}{\mid}}{CH}}$ | " | " | " | $Cl^-$ | brown |
| 15 | 2,6-Di-chloro-4-nitrophenyl | $C_4H_8$ | " | " | $C_4H_8-O-CH_2-\underset{\underset{-CH_2-O-C_2H_5}{\mid}}{\overset{\overset{OH}{\mid}}{CH}}$ | " | " | " | $Cl^-$ | " |
| 16 | 2,6-Di-chloro-4-nitrophenyl | $C_2H_4$ | " | " | $C_2H_4-O-CH_2-\underset{\underset{-CH_2-O-C_2H_5}{\mid}}{\overset{\overset{CH_3}{\mid}}{C}}-\underset{OH}{\mid}$ | " | " | " | $Cl^-$ | " |
| 17 | 2,5-Di-chloro-4-methyl-amino-sulphonyl-phenyl | $C_2H_4$ | $C_2H_5$ | $CH_3$ | $(C_2H_4-O)_2-CH_2-\underset{\underset{OH}{\mid}}{CH}-CH_3$ | $CH_3$ | H | H | $Cl^-$ | orange |
| 18 | 4-Methyl sulpho-nyl-2-chloro-phenyl | " | " | " | $(C_2H_4-O)_3-H$ | " | " | " | $Cl^-$ | " |
| 19 | 4-Methyl-sulpho-nyl-2-chloro-phenyl | " | " | " | $C_2H_4-O-CH_2-\underset{\underset{OH}{\mid}}{\overset{\overset{C_2H_5}{\mid}}{C}}-CH_3-O-CH_3$ | " | Cl | H | $Cl^-$ | " |

-continued

| No. | D | A | $R_1$ | $R_2$ | $R_3$ | $R_4$ | $R_5$ | $R_6$ | $An^{(-)}$ | Colour shade |
|-----|---|---|-------|-------|-------|-------|-------|-------|------------|--------------|
| 20 | 3-Phenyl-1,2,4-thiadiazolyl(5) | " | " | " | $CH_2-CH-CH_2-O-$<br>       $\|$<br>       $OH$<br>$(C_2H_4-O)_2-CH_3$ | $NH_2$ | H | " | $H_2PO_4^-$ | red |
| 21 | 3-Phenyl-1,2,4-thiadiazolyl(5) | " | " | " | $CH_2-CH-CH_2-O-$<br>       $\|$<br>       $OH$<br>$C_2H_4-O-C_3H_7$ | $CH_3$ | " | " | " | " |
| 22 | 3-Phenyl-1,2,4-thiadiazolyl(5) | " | " | " | $C_2H_4-O-CH_2-CH-$<br>                    $\|$<br>                    $OH$<br>$CH_2-O-C_2H_5$ | " | $CH_3$ | " | " | " |
| 23 | 3-Phenyl-1,2,4-Thiadiazolyl(5) | $C_2H_4$ | $C_2H_5$ | $CH_3$ | $C_2H_4-O-CH_2-CH$<br>                    $\|$<br>                    $OH$<br>$-CH_2-O-C_2H_5$ | $CH_3$ | H | H | $H_2PO_4^-$ | red |
| 24 | 5-Nitro-1,3-thiazolyl(2) | " | " | " | $C_2H_4-O-CH_2-CH$<br>                    $\|$<br>                    $Br$<br>$-CH_2-O-CH_2-CN$ | " | " | " | $HSO_4^-$ | " |
| 25 | 5-Nitro-1,3-thiazolyl(2) | $C_3H_6$ | " | $C_2H_5$ | $CH_2-CH-CH_2-O-$<br>       $\|$<br>       $OH$<br>$C_2H_4-OH$ | $C_2H_5$ | $CH_3$ | " | " | violet |
| 26 | 2,4-Dinitrophenyl | $C_2H_4$ | " | $CH_3$ | $CH_2-CH-CH_2-O-$<br>       $\|$<br>       $OH$<br>$(C_2H_4-O)_2-CH_3$ | $CH_3$ | " | " | " | red |
| 27 | 2,5-Dichloro-4-cyanophenyl | " | " | " | $CH_2-CH-CH_2-O-$<br>       $\|$<br>       $O-CO-C_2H_5$<br>$C^2H_4-O-CH_3$ | " | H | " | $Cl^-$ | scarlet |
| 28 | 4-Benzoylphenyl | " | " | " | $CH_2-CH-CH_2-O-$<br>       $\|$<br>       $OH$<br>$CH_2-CH-CH_3$<br>       $\|$<br>       $OH$ | " | " | " | $Cl^-$ | yellow |
| 29 | 4-Benzoylphenyl | $C_2H_4$ | $C_2H_5$ | $CH_3$ | $\quad\quad CH_3$<br>$C_2H_4-O-CH-CH-$<br>                        $\|$<br>                        $OH$<br>$-CH_2-O-CH_3$ | $CH_3$ | H | H | $Cl^-$ | yellow |
| 30 | 4-Benzoylphenyl | " | " | " | $CH_2-CH-CH_2-O-$<br>       $\|$<br>       $OH$<br>$C_2H_4-O-\langle\rangle-Cl$ | " | " | " | $Cl^-$ | " |
| 31 | 2-Cyano-4-nitrophenyl | " | " | " | $CH_2-CH-CH_2-O-$<br>       $\|$<br>       $OH$<br>$-CO-CH_2-O-C_2H_4$<br>$-O-CH_3$ | " | " | " | $Cl^-$ | red |
| 32 | 2-Cyano-4-nitrophenyl | " | " | " | $C_2H_4-O-C_2H_4-$<br>$COO-CH_2-CH-CH_2$<br>                    $\|$<br>                    $OH$<br>$-O-C_2H_5$ | " | " | " | $Cl^-$ | " |

EXAMPLE 4

28.5 g of the diazo component of the formula

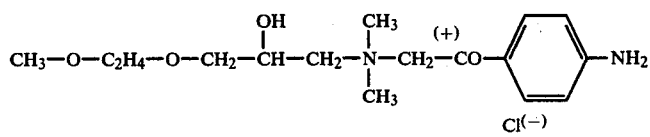

are dissolved in dilute hydrochloric acid and diazotised at 0° C. by addition of 7 g of sodium nitrite. After about 30 minutes, excess nitrite is removed by adding a little sulphamic acid, a solution of 13.1 g of 2-methylindole, dissolved in glacial acetic acid, is added dropwise whilst stirring, and the mixture is slowly neutralised to pH 5-6 with sodium hydroxide solution. After completion of the reaction, the mixture is rendered alkaline with sodium hydroxide solution, the salt solution is decanted off the dyestuff which has precipitated, and the dyestuff is washed free from salt and brought to pH 4 with water and glacial acetic acid, the amounts being chosen so as to give an approximately 40% strength yellow solution of the dyestuff of the formula

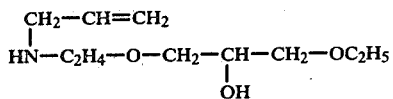

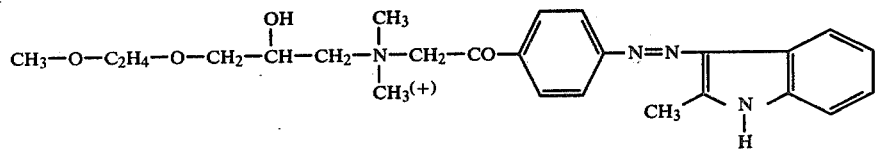

$(Cl^{(-)}, CH_3—COO^{(-)})$

EXAMPLE 5

38 g of the compound

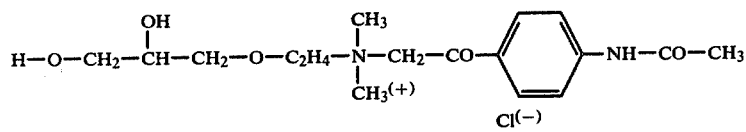

are boiled in about 10% strength aqueous hydrochloric acid for ½ hour and are then processed further as in Example 1, using a solution of 16.3 g of diethyl-m-toluidine in aqueous hydrochloric acid. A highly concentrated aqueous solution of a red dyestuff of the formula

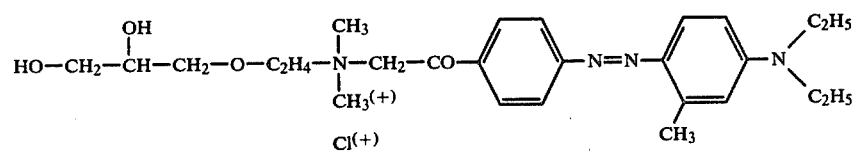

is obtained.

EXAMPLE 6

21.4 parts of 1-acetylamino-4-chloroacetylbenzene are reacted at room temperature with an aqueous solution of the compound for 24 hours whilst stirring, 4 g of sodium hydroxide are added, the excess amine is removed in vacuo, about 100 cm³ of water are added and about 15 g of dimethyl sulphate are added dropwise at 70°–90° C. From three onwards, the procedure followed is as in Example 5. A highly concentrated red solution of the dyestuff of the formula

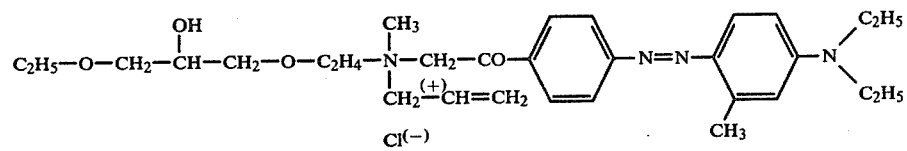

is again obtained.
The dyestuffs of the formula

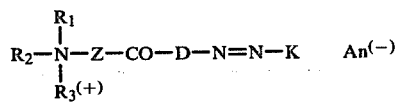

shown in the table are also obtained in accordance with the methods of Examples 4 and 5.

| No. | $R_1$ | $R_2$ | $R_3$ | Z | D | K | An | Colour shade |
|---|---|---|---|---|---|---|---|---|
| 1 | CH₃—O—CH₂—C(CH₃)(OH)—CH₂—O—C₄H₈ | CH₃ | CH₂—CH=CH₂ | CH₃—CH | 2,6-dicyano-4-methylphenyl | 4-methyl-N,N-diethylaniline | Cl⁻ | violet |
| 2 | C₂H₅—O—CH₂—CH(O—CO—CH₃)—CH₂—O—C₂H₄ | " | CH₃ | —CH₂— | 2-cyano-3,4,6-trimethylphenyl | 4-methyl-3-chloro-N,N-diethylaniline | " | red |
| 3 | C₄H₉—O—CH₂—CH(OH)—CH₂—O—C₂H₄ | " | " | " | 4-methylphenyl | N-ethyl-N-(β-cyanoethyl)-3-methyl-4-aniline | Br⁻ | orange |
| 4 | C₆H₅—O—C₂H₄—O—CH₂—CH(OH)—CH₂; CH₃ | " | " | " | " | 2-chloro-N-(β-cyanoethyl)-4-methylaniline | Cl⁻ | yellow |
| 5 |  | " | " | " | " | N-ethyl-N-[CH₂—CH(OH)—CH₂—O—C₂H₄—O—C₄H₉]-3-methylaniline | " | red |
| 6 | " | CH₃ | " | CH₂ | " | N,N-di[CH₂—CH(Cl)—CH₂—O—C₂H₄—O—CH₃]-C₂H₄-aniline | " | " |

-continued

| No. | R₁ | R₂ | R₃ | Z | D | K | An | Colour shade |
|---|---|---|---|---|---|---|---|---|
| 7 | C₂H₅ | C₂H₅ | C₂H₅ | " | " | 3-methylphenyl-N(C₂H₅)–C₂H₄–O–CH₂–CH(Cl)–CH₂ | " | " |
| 8 | CH₂=CH–CH₂– | CH₃ | CH₃ | " | " | 3-methylphenyl-N(CH₃)– with –O–CH₃ substituent | " | " |
| 9 | HO–CH₂–CH(OH)–CH₂–O–C₂H₄– | " | " | " | " | 3-methylphenyl-N(CH₃)–CH₂–CH(OH)–CH₂–O–C₂H₄–OH | " | " |
| 10 | | " | " | " | " | cyclohexyl-pyrazolone (CH₃, N=N, C=O, OH) | " | yellow |
| 11 | C₂H₅–O–CH₂–CH(OH)–CH₂–O–CO–C₂H₄–O–C₂H₄ | " | " | " | " | 3-methylphenyl-N(C₂H₅)₂ | " | red |
| 12 | CH₃–O–C₂H₄–O–CH₂–CO–O–CH₂–CH(OH)–CH₂ | " | " | " | " | phenyl-N(C₂H₅)₂ | " | " |

EXAMPLE 7

90 g of 6-methoxy-2-aminobenzthiazole are dissolved in a mixture of 350 g of glacial acetic acid and 150 g of propionic acid at 20° C. (duration about ½ hour). The mixture is then cooled to 0° C. and 55 cm³ of nitrosylsulphuric acid (100 cm³ contain 42 g of nitrite) are added dropwise in the course of one hour at 0° to −3° C., with good stirring. In the course thereof, the temperature should not fall below −3° C. The resulting diazo solution is poured, whilst stirring, into a solution of 11.5 g of the base of the formula

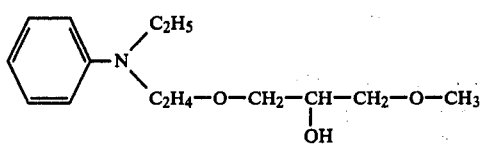

in 1,700 cm³ of water, 33 cm³ of concentrated sulphuric acid and 700 g of ice. The temperature is kept at 0° C. The mixture is then neutralised with 280 cm³ of 45% strength sodium hydroxide solution. The temperature is kept below 5° C. by adding a further 700 g of ice. Stirring is continued overnight and the dyestuff is then filtered off and washed until neutral. The resulting red dyestuff can be quaternised in the following ways:

(a) 207 g of the dyestuff are introduced into 250 cm³ of dimethylformamide whilst stirring at 75° to 80° C., and 75 g of dimethyl sulphate are added. Hereupon, the colour shade changes from red to blue. 120 g of dimethylformamide are then distilled off in vacuo at 15 mm Hg. The residue is cooled to 20° C., whilst stirring, and 325 cm³ of toluene are added slowly in the course of ½ hour. Hereupon, the dyestuff precipitates. Stirring is then continued overnight, after which the product is thoroughly suction-drained or the liquor is decanted, and the product is rinsed with 75 cm³ of toluene. The dyestuff has the formula:

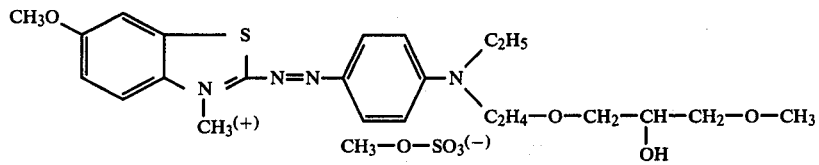

Adhering residues of toluene are removed by drying in vacuo or by blowing off with steam. The dyestuff goes pasty on addition of even a little water. Equal parts of dyestuff and water give a solution which is also readily stable and which is best rendered slightly acid with a little acetic acid. Solutions containing more than 50% of dyestuff can also be prepared. To prepare a powder formulation, an aqueous solution, adjusted to pH 5, is provided with the desired amount of extender, for example dextrin, and is then spray-dried. The formulation can also be produced by grinding the dyestuff with dextrin.

(b) 207 g of the dyestuff are introduced into 1,000 cm³ of chlorobenzene whilst stirring at 80° to 90° C., a few cm³ of chlorobenzene are distilled off until no further water passes over, and 78 g of dimethyl sulphate are added. The mixture is stirred for about 8 hours at 90° to 95° C. Hereupon, the colour shade changes from red to blue and the reaction product precipitates. The chlorobenzene is distilled off in vacuo in order to remove the excess dimethyl sulphate, and the remainder is then blown off with steam in vacuo. The aqueous dyestuff solution which remains can, as described under (a), be used as such or be converted to a powder dyestuff by spray drying.

(c) The quaternisation of the dyestuff can also be effected by simultaneous addition of dimethyl sulphate and sodium acetate to the dyestuff, dispersed in water at 0° to 15° C., whilst maintaining a pH value of about 4 to 5.

EXAMPLE 8

41.4 parts of the compound of the formula

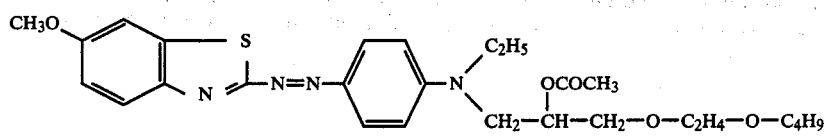

are dissolved in 460 parts of glacial acetic acid whilst stirring, and the solution is warmed to 40°–45° C. 53 parts of ethylene oxide are passed into the solution in the course of 2 hours and the latter is stirred for a further 3 hours at 50°–60° C. Thereafter, 16 parts of 35% strength hydrochloric acid are added and the glacial acetic acid is distilled off in vacuo. The residue is dissolved in about 200 parts of water and stirred thoroughly with about 5 g of active charcoal, the resulting solution is filtered and the blue dyestuff is salted out with sodium chloride. It separates out as a liquid which is separated from the aqueous phase. The liquid dyestuff thus obtained still contains a little water and is miscible therewith in all proportions. It has the formula

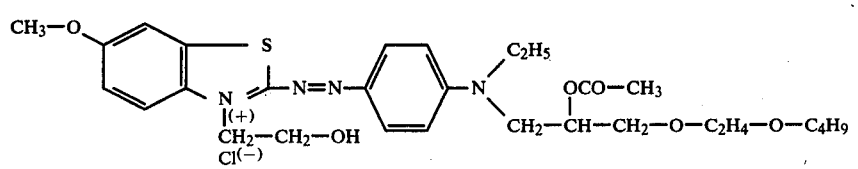

EXAMPLE 9

10 parts in 35% strength hydrochloric acid are added to a mixture of 41.4 parts of the compound of the formula

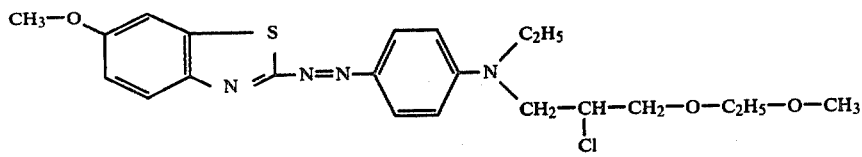

and of 35 parts of acrylamide in 50 parts of glacial acetic acid, and the mixture is stirred at 90° C. for about 2 hours. The glacial acetic acid is then distilled off in vacuo, the residue is dissolved in about 200 parts of water, the mixture is thoroughly stirred with about 5 g of active charcoal and filtered, and the blue dyestuff is salted out with sodium chloride; it separates out as a liquid and is separated off. The resulting dyestuff contains water and is miscible with water in all proportions. It has the formula

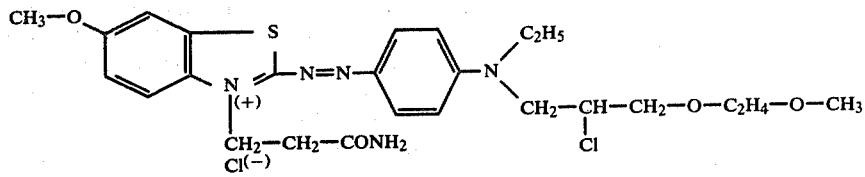

The table which follows shows dyestuffs of the formula

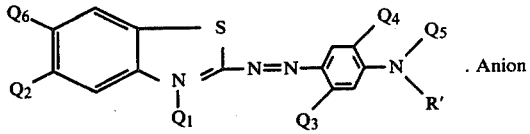

These can be prepared in accordance with the methods described above.

| No. | Q₁ | Q₂ | Q₃ | Q₄ | Q₅ | Q₆ | R | An |
|---|---|---|---|---|---|---|---|---|
| 1 | $CH_3$ | $CH_3-O$ | H | H | $C_2H_5$ | H | $CH_2-CH(OH)-CH_2-O-C_2H_4-O-C_4H_9$ | $CH_3-COO^-$ |
| 2 | " | " | " | " | " | " | $C_4H_8-O-CH_2-CH(OH)-CH_2-O-C_2H_5$ | $Cl^-$ |
| 3 | " | " | $CH_3$ | " | $CH_3$ | " | $C_2H_4-O-CH_2-CH(OH)-CH_2-O-CH_3$ | " |
| 4 | " | " | $O-CH_3$ | " | $C_2H_4-CN$ | " | $CH_2-CH(O-CO-CH_3)-CN_2-O-(C_2H_4-O)_2-CH_3$ | $CH_3-SO_4^-$ |
| 5 | " | " | H | " | $C_2H_5$ | " | $CH_2-CH(Cl)-CH_2-O-C_2H_4-OH$ | " |
| 6 | " | (methylphenyl group) | " | " | " | " | $CH_2-CH(OH)-CH_2-O-CH_2-CH_3$ | " |
| 7 | " | (2-methoxyphenyl group) | " | " | " | " | $C_2H_4-O-CH_2-CH(OH)-O-C_6H_5$ | " |
| 8 | " | " | " | " | " | " | $CH_2-CH(OH)-CH_2-O-CO-CH_2-O-C_6H_5$ | " |
| 9 | " | " | " | " | " | " | $C_2H_4-O-C_2H_4-COO-CH_2-CH(OH)-CH_2-O-C_2H_5$ | " |
| 10 | " | $CH_3-O-CH_2-CH(OH)-CH_2-O-C_2H_4$ | " | " | " | " | $C_2H_5$ | $HSO_4^+$ |
| 11 | " | $C_6H_5-O-C_2H_4-O-CH_2-CH(OH)-CH_2$ | " | " | " | " | | " |

EXAMPLE 10

8.4 g of 3-amino-1,2,4-triazole are dissolved in 400 cm$^3$ of water and 20 cm$^3$ of concentrated hydrochloric acid and 7 g of sodium nitrite dissolved in 50 cm$^3$ of water are added dropwise at 0° C. whilst stirring. 16.5 g of the base of the formula

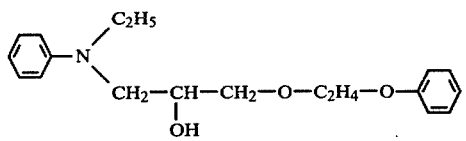

dissolved in dilute hydrochloric acid are added, whilst stirring. Thereafter the mixture is neutralised with 45% strength sodium hydroxide solution and the dyestuff which has precipitated is filtered off and dried.

124 g of the dyestuff are introduced into 250 cm$^3$ of dimethylformamide at 75° to 80° C., whilst stirring, and 150 g of dimethyl sulphate are added. Hereupon, the colour shade changes from yellow to red. 120 g of dimethylformamide are then distilled off in vacuo at 15 mm Hg. The residue is cooled to 20° C., whilst stirring, and 325 cm$^3$ of toluene are added slowly in the course of ½ hour. Hereupon, the dyestuff precipitates. Stirring is continued overnight, the product is allowed to sediment, the solvent mixture is decanted off, the product is again stirred with toluene, the latter is decanted off and the residual toluene is blown off with steam. A stable dyestuff solution remains, which can be employed, as such, for dyeing. The dissolved dyestuff is miscible with water in all proportions.

The dyestuffs of the formula

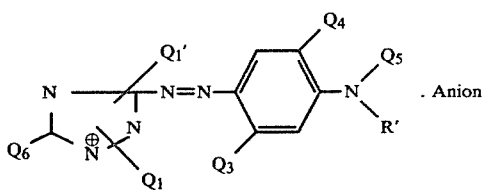

shown in the table can also be prepared in accordance with these processes. They dye polyacrylonitrile in a red colour shade.

| No. | $Q_1$ | $Q_3$ | $Q_4$ | $Q_5$ | $Q_6$ | R' | An | $Q_1'$ |
|---|---|---|---|---|---|---|---|---|
| 1 | $CH_3$ | H | H | $C_2H_5$ | H | $C_4H_8-O-CH_2-CH(OH)-CH_2-O-\text{(4-methylphenyl)}$ | $Cl^-$ | $CH_3$ |
| 2 | $C_2H_5$ | $CH_3$ | " | $C_3H_7$ | " | $CH_2-CH(Cl)-CH_2-O-C_2H_4-O-C_4H_9$ | " | $C_2H_5$ |
| 3 | $CH_3$ | " | " | $C_2H_5$ | " | $CH_2-CH(O-CO-CH_3)-CH_2-O-C_2H_4-O-\text{phenyl}$ | " | $CH_3$ |
| 4 | " | H | " | " | " | $C_2H_4-O-CH_2-CH(Cl)-CH_2-O-\text{cyclohexyl}$ | $CH_3SO_4^-$ | " |
| 5 | " | " | " | " | " | $C_2H_4-O-CH_2-CH(OH)-CH_2-C_2H_5$ | " | " |
| 6 | " | " | " | " | " | $C_2H_4-O-CH_2-CH(Br)-CH_2-O-\text{phenyl}$ | " | " |
| 7 | " | " | " | $CH_2-CH=CH_2$ | $CH_2-CH(OH)-CH_2-O-C_2H_4OCO-\text{phenyl}$ | $CH_2=CH_2$ | " | " |
| 8 | $CH_3$ | H | H | $CH_2-CH=CH_2$ | $CH_2-O-C_2H_4-O-CH_2-CH(OH)-C_2H_5$ | $C_2H_5$ | $CH_3SO_4^-$ | $CH_3$ |
| 9 | $CH_3$ | H | H | $\text{phenyl}$ | H | $CH_2-CH(OH)-CH_2-O-C_2H_4-O-C_4H_9$ | $CH_3SO_4^-$ | $CH_3$ |
| 10 | " | " | " | $C_2H_5$ | " | $C_2H_4-COO-CH_2-CH_2-O-C_2H_4-O-\text{phenyl}$ | " | " |
| 11 | " | " | " | " | " | $CH_2-CH(OH)-CH_2-O-CO-CH_2-O-C_2H_4-O-\text{(4-chlorophenyl)}$ | " | " |

EXAMPLE 11

18.15 parts by weight of 5-chloro-1-methylbenzimidazole in 300 parts by volume of water and 60 parts by volume of 5 N hydrochloric acid are diazotised in the usual manner with 20.5 parts by volume of 5 N sodium nitrite solution at 0° to 5° C. The diazo solution is added dropwise to a solution of 23 parts by weight of the base of the formula

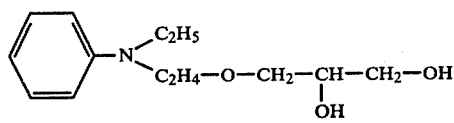

in 50 parts by weight of glacial acetic acid and 200 parts by volume . . . , whilst stirring, the stirring is continued until the coupling reaction has ended, the mixture is rendered alkaline with sodium hydroxide solution, the aqueous solution is decanted off, the product is washed in the same manner with water until free from salt, 500 parts by volume of toluene are added and the residual water is distilled off azeotropically. 10 parts by volume of dimethyl sulphate are added to the dyestuff solution in toluene, thus obtained, at 90° C., the mixture is stirred until quaternisation is complete, the toluene is blown off with steam and a highly concentrated aqueous dyestuff solution is obtained, which—when adjusted to pH 4—can be used as a liquid formulation or can be converted, with addition of extenders, to a powder formulation, for example by spray drying. The red dyestuff has the formula

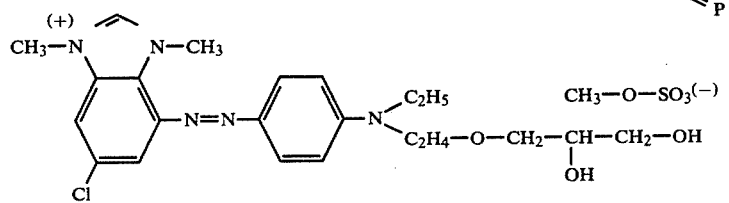

EXAMPLE 12

16.9 g of 5-chloro-7-aminobenztriazole are dissolved in 60 cm$^3$ of 78% strength sulphuric acid and diazotised with 16 cm$^3$ of 43.5% strength nitrosylsulphuric acid at about 10° C. in the course of 15 minutes. The mixture is stirred for a further 60 minutes at 10°–20° C. and the diazo solution is then introduced into a mixture of 400 g of ice and 100 cm$^3$ of water, whilst stirring. The excess nitrite is removed by adding amidosulphonic acid. The diazo solution is then clarified with a little kieselguhr and animal charcoal and is stirred into a solution of 23 g of the base of Example 8 in 50 cm$^3$ of glacial acetic acid and 200 g of water. After about 2 hours, the coupling reaction has ended. The mixture is rendered weakly alkaline with sodium hydroxide solution, the salt solution is decanted off, the product is washed in the same manner with water until free from salt, 70 cm$^3$ of dimethylformamide are added, about 15 cm$^3$ are distilled off in vacuo, 8 g of dimethyl sulphate are added and the mixture is warmed to 75°–85° C., whilst stirring, until the quaternisation and alkylation has ended. 25 cm$^3$ of the dimethylformamide are then distilled off at 15 mm Hg. The residue is cooled to 20° C., whilst stirring, and 65 cm$^3$ of toluene are added slowly in the course of ½ hour. Hereupon, the dyestuff precipitates. The dimethylformamide/toluene mixture is decanted off, the dyestuff is twice extracted by stirring with toluene in the same manner, and the toluene still remaining after decanting off is blown off with steam in vacuo. A solution of the red-violet dyestuff of the formula

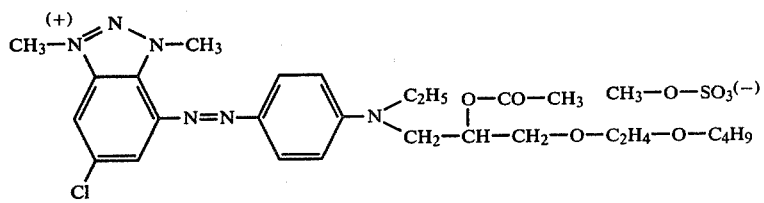

remains.

The dyestuffs of the formula

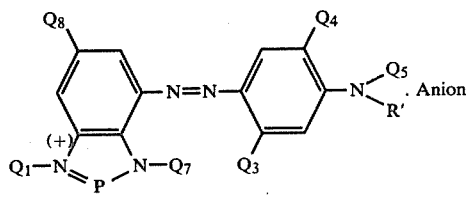

shown in the table can also be prepared by this method.

| No. | Q1 | Q3 | Q4 | Q5 | Q8 | Q7 | R' | P | An | Colour shade |
|---|---|---|---|---|---|---|---|---|---|---|
| 1 | CH$_3$ | H | H | C$_2$H$_5$ | Cl | CH$_3$ | C$_4$H$_8$—O—CH$_2$—CH—CH$_2$—O—C$_2$H$_5$<br>　　　　　　　　　　　　　＼OH | CH | CH$_3$SO$_4^-$ | red |
| 2 | C$_2$H$_5$ | " | " | " | " | C$_2$H$_5$ | CH$_2$—CH—CH$_2$—O—CH$_2$—CH—CH$_3$<br>　　　＼OH　　　　　　　　　　＼OH | N | C$_2$H$_5$SO$_4^-$ | red-violet |
| 3 | " | " | " | " | " | " | CH$_2$—CH—CH$_2$—O—C$_2$H$_4$—O—⌬<br>　　　＼OH | " | C$_2$H$_5$SO$_4^-$ | red-violet |
| 4 | CH$_3$ | CH$_3$ | " | C$_2$H$_4$—CN | " | C$_2$H$_4$—O—CH$_2$—CH—CH$_2$—⌬<br>　　　　　　　　　　＼OH | C$_2$H$_5$ | CH | CH$_3$SO$_4^-$ | red |
| 5 | " | " | " | CH$_3$ | " | CH$_3$ | C$_2$H$_4$—O—CH$_2$—CH—CH$_2$—⌬<br>　　　　　　　　　　＼Cl | " | " | " |
| 6 | " | " | " | " | " | " | CH$_2$—CH—CH$_2$—O—(C$_2$H$_4$—O)$_2$—C$_3$H$_7$<br>　　　＼O—CO—CH$_3$ | " | " | " |
| 7 | " | " | " | " | " | " | CH$_2$—CH—CH$_2$—O—CO—CH$_2$—O—C$_2$H$_4$—O—C$_2$H$_5$<br>　　　＼OH | " | " | " |
| 8 | " | O—CH$_3$ | " | " | " | " | C$_2$H$_4$—CO—O—CH$_2$—CH—CH$_2$—O—C$_2$H$_4$—O—C$_2$H$_5$<br>　　　　　　　　　　　　　＼OH | " | " | " |
| 9 | " | H | " | " | " | " | C$_2$H$_4$—O—CH$_2$—CH—CH$_2$—O—CO—C$_2$H$_4$—O—C$_2$H$_4$—O—CH$_3$<br>　　　　　　　　　　＼Cl | " | " | orange |

EXAMPLE 13

112 parts of 5-nitro-1,2-dimethyl-indazolone-3-hydrazone are coupled, in the presence of sodium chlorite, with 110 parts of the base of the formula

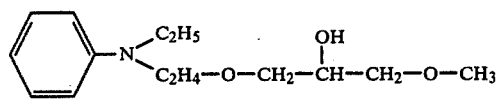

The resulting dyestuff, in a total volume of about 2,000 parts of water, is rendered alkaline with sodium bicarbonate, at 55° C. The mixture is allowed to cool, whilst stirring and is stirred for a further 12 hours, the aqueous solution is decanted off, the product is neutralised to pH 4 with dilute aqueous acetic acid and an aqueous solution of a blue dyestuff of the formula

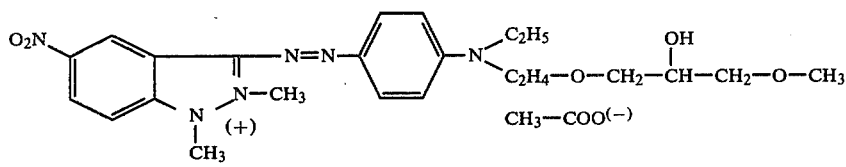

is obtained.

EXAMPLE 14

13.3 parts of 3-aminoindazole in 100 parts of water and 50 parts of concentrated hydrochloric acid are diazotised with 6.9 parts of sodium nitrite at 0° to 5° C. and coupled, in acid solution, with 22.3 parts of the base from Example 13. The solution is rendered weakly alkaline with sodium carbonate, the salt solution is decanted off the dyestuff which has precipitated and the dyestuff is freed from the residual salt in the same manner, using water. 70 parts of dimethylformamide are then added, about 15 cm³ are distilled off in vacuo, 8 parts of dimethyl sulphate are added and the mixture is warmed to 75°–85° C., whilst stirring, until the quaternisation and alkylation has ended. Thereafter, 25 parts of dimethylformamide are distilled off at 15 mm Hg. The residue is cooled to 20° C., whilst stirring, and 65 parts of toluene are added in the course of ½ hour. The solvent mixture is decanted off the dyestuff which has precipitated, the dyestuff is twice protruded with toluene and the toluene which has remained after decanting is blown off with steam. A dyestuff solution having a red-violet colour remains. The dyestuff has the formula

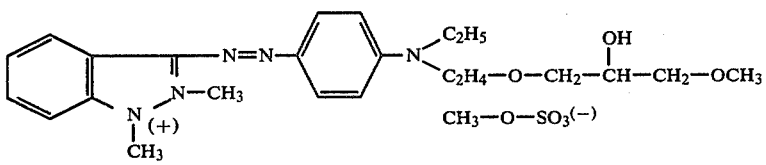

The dyestuffs of the formula

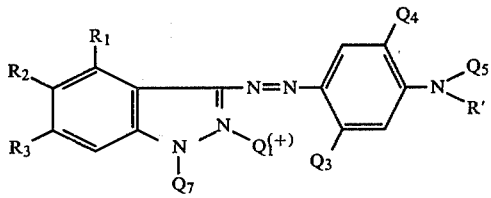

shown in the table can also be prepared in accordance with processes 13 and 14.

| No. | Q₁ | Q₃ | Q₄ | Q₅ | R₁ | R₂ | R₃ | Q₇ | R' | An | Colour shade |
|---|---|---|---|---|---|---|---|---|---|---|---|
| 1 | CH₃ | NH—CO—CH₃ | H | H | H | H | NO₂ | C₂H₄—O—CH₂—CH—CH₂—O—C₄H₉<br>                        O—CO—CH₃ | H | CH₃SO₄⁻ | red |
| 2 | " | NH—CO—CH₂—O—(C₂H₄—O—)₂—C₆H₅<br>            CH₃ | " | " | " | " | " | CH₃ | " | " | " |
| 3 | " | " | " | C₂H₅ | " | NO₂ | H | " | CH₂—CH—CH₂—O—C₂H₄—O—C₆H₅<br>      OH | " | blue |
| 4 | " | H | " | " | " | " | " | " | C₂H₄—O—CH₂—CH—CH₂—O—C₄H₉<br>               OH | " | " |
| 5 | C₂H₅ | " | " | C₃H₇ | " | H | " | C₂H₅ | C₄H₈—O—CH₂—CH—CH₂<br>              OCH₃<br>              O—CO—CH₃ | " | violet |
| 6 | CH₃ | " | " | CH₃ | " | " | " | CH₃ | CH₂—CH—CH₂—O—C₂H₄—O—C₆H₅<br>      Cl | Cl⁻ | " |
| 7 | " | " | " | " | " | " | " | " | CH₂—CH—CH₂—O—C₂H₄—O—CO—C₆H₅<br>      Br | " | " |
| 8 | " | " | " | C₂H₅ | " | " | " | " | C₂H₄—COO—CH₂—CH—CH₂—O—C₂H₄—O—CH₃<br>                     OH | " | " |
| 9 | " | " | " | " | " | " | " | " | CH₂—CH—CH₂—OCO—CH₂—O—C₂H₄—OH<br>      OH | " | " |

EXAMPLE 15

A polyacrylonitrile fabric is printed with a printing paste which has been prepared in the following manner:

30 parts of the dyestuff described in Example 1 are covered with 330 parts of hot water and the resulting solution is added to 500 parts of crystal gum (gum arabic as a thickener). Finally, 30 parts of zinc nitrate solution are also added. The resulting print is dried, steamed for 30 minutes and then rinsed. A blue print having very good fastness properties is obtained.

EXAMPLE 16

Acid-modified polyethylene glycol terephthalate fibres are introduced, using a liquor ratio of 1:40, into an aqueous bath, at 20° C., which contains, per liter, 3 to 10 g of sodium sulphate, 0–15 g of dimethylbenzyl-dodecylammonium chloride and 0.15 g of the dyestuff described in Example 2, and has been adjusted to pH 4–5 with acetic acid. The bath is heated to 100° C. in the course of 30 minutes and is kept at this temperature for 60 minutes. Thereafter, the fibres are rinsed and dried. A blue dyeing having very good fastness properties is obtained.

EXAMPLE 17

Polyacrylonitrile fibres are introduced, using a liquor ratio of 1:40, into an aqueous bath, at 40° C., which contains, per liter, 0.75 g of 30% strength acetic acid, 0.38 g of sodium acetate and 0.15 g of the dyestuff described in Example 1. The bath is heated to the boil in the course of 20–30 minutes and kept at this temperature for 30–60 minutes. After rinsing and drying, a blue dyeing having very good fastness properties is obtained.

EXAMPLE 18

A stock solution is prepared from 15 parts by weight of the dyestuff mentioned in Example 1, 15 parts by weight of polyacrylonitrile and 70 parts by weight of dimethylformamide and is heated to a customary polyacrylonitrile spinning solution and spun in the known manner. A blue dyeing having very good fastness properties is obtained.

EXAMPLE 19

Acid-modified synthetic polyamide fibres are introduced, using a liquor ratio of 1:40, into an aqueous bath, at 40° C., which contains, per liter, 10 g of sodium acetate and 0.3 g of the dyestuff described in Example 1 and has been adjusted to pH 4–5 with acetic acid. The bath is heated to 98° C. in the course of 30 minutes and is kept at this temperature. The fibres are then rinsed and dried. A blue dyeing is obtained.

I claim:

1. Cationic dyestuff of the formula $$[(D-N=N-K)(-R)_n]^{m \oplus} {}_{mo}An^{\ominus}$$

wherein

D is a phenyl, thiazolyl, benzthiazolyl, benzisothiazolyl, thiadiazolyl, pyrazolyl, indazolyl, imidazolyl, benzimidazolyl, triazolyl, benztriazolyl, pyridinyl, pyrazolopyridinyl, quinolinyl, or benzoxazolyl radical;

K is a phenyl naphthyl, indolyl, aminopyrazolyl, dihydroindolyl, pyrazolyl, pyrazolonyl, indazolyl, imidazolyl; benzimidazolyl, benztriazolyl, benzisothiazolyl, benzthiazolyl, tetrahydroquinolinyl, or malonodintrilo radical; or the radical of a coupling component selected from the group consisting of acetoacetate, cyanoacetate, cyanoacetic acidamide and acetoacetic acid amide;

m and n independently of one another are 1 or 2;

$An^{\ominus}$ is an anion;

R is

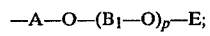

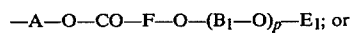

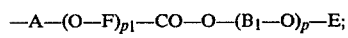

A is $C_2$–$C_4$-alkylene unsubstituted or substituted with halogen, hydroxyl, $C_1$–$C_4$-alkoxy, or $C_1$–$C_4$-alkoxycarbonyl; or a direct bond;

$B_1$ is $C_2$–$C_4$-alkylene; or $C_2$–$C_4$-alkylene substituted by halogen, $C_1$–$C_4$-alkoxy, hydroxyl, or $C_1$–$C_4$-alkoxycarbonyl;

E is $C_1$–$C_6$-alkyl; $C_2$–$C_6$-alkenyl; $C_1$–$C_6$-alkyl substituted by cyano, halogen or $C_1$–$C_4$-alkoxy; cyclohexyl; cyclopentyl; cyclohexyl or cyclopentyl substituted by methyl; formyl; ($C_1$–$C_6$-alkyl)-carbonyl; ($C_2$–$C_6$-alkenyl)-carbonyl; ($C_1$–$C_6$-alkyl)carbonyl substituted in the alkyl group by cyano, halogen, or $C_1$–$C_4$-alkoxy; hydrogen; phenylcarbonyl; phenyl-($C_1$–$C_6$-alkyl)-carbonyl; phenyloxy-($C_1$–$C_6$-alkyl)-carbonyl; phenyl-($C_1$–$C_6$-alkyl)-phenyl; or phenylcarbonyl, phenyl-($C_1$–$C_6$-alkyl)-carbonyl, phenyloxy-($C_1$–$C_6$-alkyl)-carbonyl, phenyl-($C_1$–$C_6$-alkyl), or phenyl substituted in the phenyl by 1 or 2 members selected from the group consisting of $C_1$–$C_4$-alkyl, $C_1$–$C_4$-alkoxy and halogen; wherein the alkenyl groups are straight-chain or branched;

F is $C_1$–$C_6$-alkylene;

p is 1 to 3; and $p_1$ is 0 or 1;

and wherein at least one of the radicals A or $B_1$ is substituted.

2. Cationic dyestuff of claim 1 of the formula

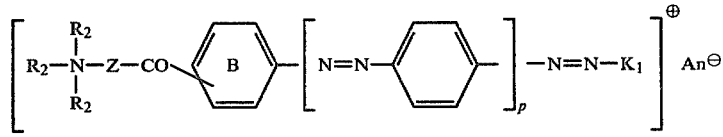

wherein $R_2$ is hydrogen; R; $C_1$–$C_6$-alkyl; $C_1$–$C_6$-alkenyl; $C_1$–$C_6$-alkyl or $C_2$–$C_6$-alkenyl substituted by halogen, cyano, aminocarbonyl, hydroxyl, $C_1$–$C_4$-alkoxy, $C_1$–$C_3$-alkoxy-carbonyl, $C_1$–$C_3$-alkylcarbonyloxy or phenoxy; benzyl; phenylethyl; benzyl or phenylethyl substituted by halogen, $C_1$–$C_4$-alkoxy, $C_1$–$C_4$-alkyl, or R; or one $R_2$ is $N(R_2)_2$; or two radicals $R_2$ conjointly are tetramethylene, pentamethylene or 3-aza- or 3-oxa-pentamethylene;

Z is $C_1$–$C_3$-alkylene;

$K_1$ is the radical of a benzene, naphthalene, indole, pyrazolone or aminopyrazole coupling component;

p is 0 or 1; and the ring B is unsubstituted or mono- or di-substituted by $C_1$-$C_4$-alkyl, $C_1$-$C_4$-alkoxy, $C_1$-$C_4$-alkylsulphonyl, halogen, cyano, nitro or R.

3. Cationic dyestuff of claim 1 of the formula

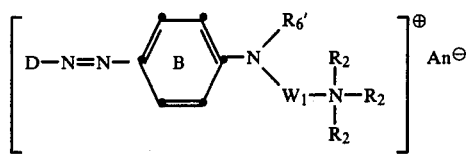

containing 1 or 2 substituents R; wherein

D is a phenyl; benzthiazolyl; benzisothiazolyl; 1,3,4-thiadiazolyl-(2); 1,2,4-thiadiazolyl-(5); 1,3-thiazolyl-(2); pyridinyl-(2); or pyridinyl-(4) radical;

$W_1$ is straight-chain or branched $C_2$-$C_5$-alkylene;

$R_6'$ is hydrogen, R, $C_1$-$C_6$-alkyl; $C_1$-$C_6$-alkyl substituted by chlorine, bromine, cyano, hydroxyl, $C_1$-$C_4$-alkoxy, $C_1$-$C_4$-alkoxycarbonyl or $C_1$-$C_4$-alkylcarbonyloxy; $C_3$-$C_4$-alkenyl; or $$\left[ -W_1-\overset{R_2}{\underset{R_2}{N}}-R_2 \right]^{\oplus} An^{\ominus};$$

or $R'_6$ with $N$-$W_1$-$N$-$R_2$ is piperazine;

$R_2$ is hydrogen; R; $C_1$-$C_6$-alkyl; $C_2$-$C_6$-alkenyl; $C_1$-$C_6$-alkyl or $C_2$-$C_6$-alkenyl substituted by halogen, cyano, aminocarbonyl, hydroxyl; $C_1$-$C_4$-alkoxy, $C_1$-$C_3$-alkoxy-carbonyl, $C_1$-$C_3$-alkylcarbonyloxy or phenoxy; benzyl; phenylethyl; benzyl or phenylethyl substituted by halogen, $C_1$-$C_4$-alkoxy, $C_1$-$C_4$-alkyl or R; or one $R_2$ is $N(R_2)_2$; or two radicals $R_2$ conjointly are tetramethylene, pentamethylene or 3-aza- or 3-oxa-pentamethylene;

and the ring B is unsubstituted or substituted by R, $C_1$-$C_5$-alkyl, $C_1$-$C_4$-alkoxy, halogen, phenyloxy, benzyloxy, $C_1$-$C_3$-alkylcarbonylamino, $C_1$-$C_3$-alkyl-sulphonylamino, $C_1$-$C_3$-alkylcarbonylamino, benzoylamino or phenylsulphonylamino.

4. The dyestuff of claim 1, wherein at least one of the radicals A or B is substituted with hydroxyl.

5. Cationic dyestuff of claim 1 of the formula

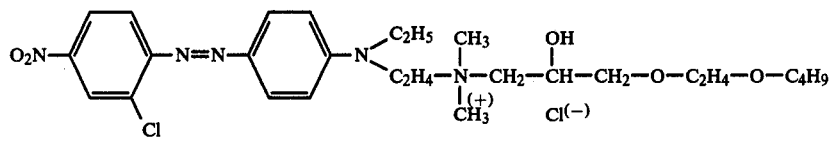

6. Cationic dyestuff of claim 1 of the formula

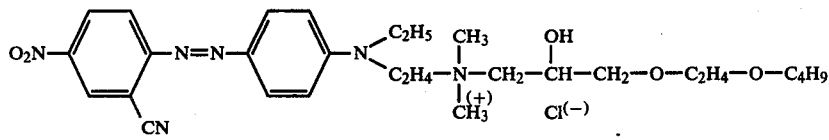

7. Cationic dyestuff of claim 1 of the formula

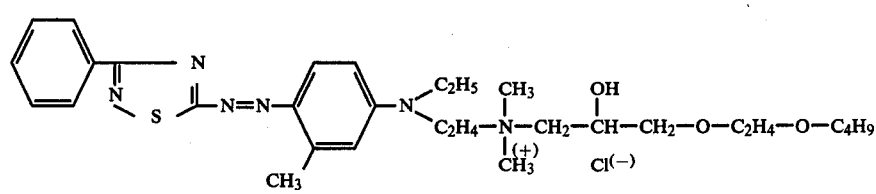

8. Cationic dyestuff of claim 1 of the formula

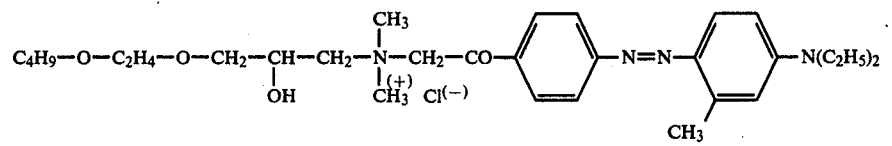

9. Cationic dyestuff of claim 1 of the formula

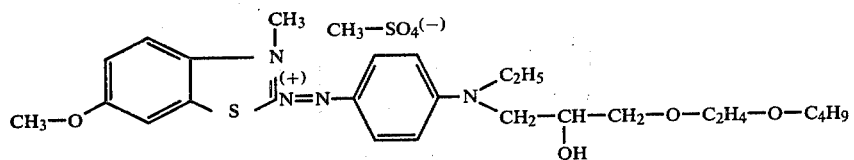
10. Cationic dyestuff of claim 1 of the formula
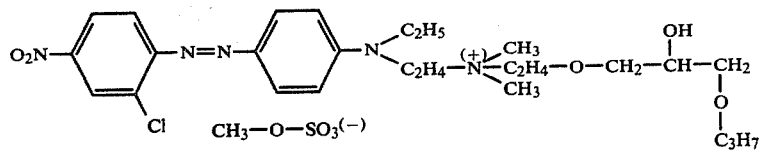
* * * * *